US011154557B2

(12) United States Patent
Gendelman et al.

(10) Patent No.: US 11,154,557 B2
(45) Date of Patent: Oct. 26, 2021

(54) ANTIVIRAL PRODRUGS AND NANOFORMULATIONS THEREOF

(71) Applicant: Board of Regents of the University of Nebraska, Lincoln, NE (US)

(72) Inventors: Howard Gendelman, Omaha, NE (US); Benson Edagwa, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 17/301,030

(22) Filed: Mar. 22, 2021

(65) Prior Publication Data

US 2021/0213023 A1 Jul. 15, 2021

Related U.S. Application Data

(63) Continuation of application No. PCT/US2019/057406, filed on Oct. 22, 2019.

(60) Provisional application No. 62/748,798, filed on Oct. 22, 2018.

(51) Int. Cl.
| | | |
|---|---|---|
| *A61K 31/535* | (2006.01) | |
| *A61K 31/495* | (2006.01) | |
| *A61K 9/50* | (2006.01) | |
| *A61K 31/5365* | (2006.01) | |
| *A61P 31/18* | (2006.01) | |
| *A61K 9/00* | (2006.01) | |
| *A61K 9/16* | (2006.01) | |

(52) U.S. Cl.
CPC ........ *A61K 31/5365* (2013.01); *A61K 9/0019* (2013.01); *A61K 9/1641* (2013.01); *A61P 31/18* (2018.01)

(58) Field of Classification Search
CPC .. A61K 31/4985; A61K 31/5365; A61P 31/18
USPC .............................. 514/250, 269, 312, 230.5
See application file for complete search history.

(56) References Cited

U.S. PATENT DOCUMENTS

| | | |
|---|---|---|
| 9,216,996 B2 | 12/2015 | Jin et al. |
| 9,758,515 B2 | 9/2017 | Takahashi et al. |
| 2013/0171214 A1 | 7/2013 | Mundhra et al. |
| 2014/0011995 A1 | 1/2014 | Sumino et al. |
| 2014/0221378 A1 | 8/2014 | Miyazaki et al. |
| 2015/0050241 A1 | 2/2015 | Volinsky et al. |
| 2015/0232479 A1 | 8/2015 | Johns et al. |
| 2017/0326103 A1 | 11/2017 | Porter et al. |

FOREIGN PATENT DOCUMENTS

| | | |
|---|---|---|
| WO | WO-2010011814 A1 | 1/2010 |
| WO | WO-2012061480 A2 | 5/2012 |
| WO | WO-2017223280 A2 | 12/2017 |

(Continued)

OTHER PUBLICATIONS

Zhou et al. "A long-acting nanoformulated cabotegravir prodrug for improved antiretroviral therapy," Topics in Antiviral Medicine, Apr. 2017 vol. 25, 1 supp. Supplement1, pp. 180s-181s. Abstract No. 439. EMBASE Document No. 616686282 (Year: 2017).*

(Continued)

*Primary Examiner* — Shengjun Wang
(74) *Attorney, Agent, or Firm* — Goodwin Procter LLP

(57) ABSTRACT

The present invention provides prodrugs and methods of use thereof.

7 Claims, 8 Drawing Sheets

(56) References Cited

FOREIGN PATENT DOCUMENTS

Figure 1A:
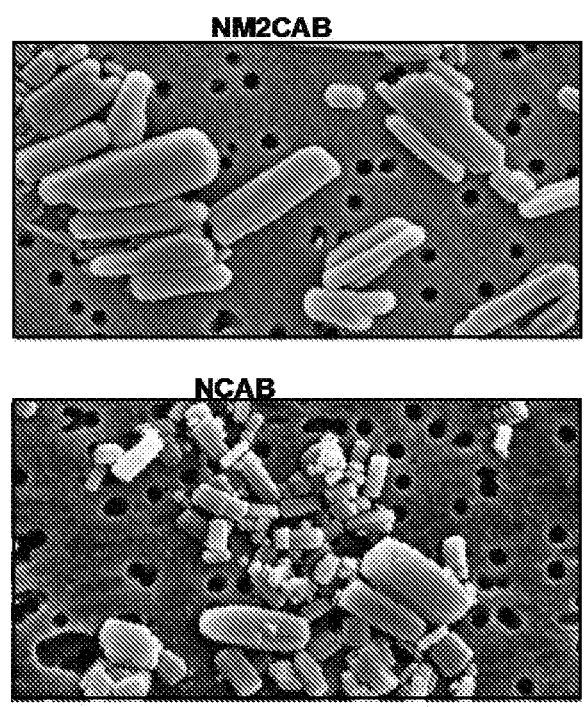

| WO | WO-2020086555 A1 | 4/2020 |
|---|---|---|
| WO | WO-2020112931 A1 | 6/2020 |

OTHER PUBLICATIONS

Zhou et al. ("A long-acting nanoformulated cabotegravir prodrug for improved antiretroviral therapy," Topics in Antiviral Medicine, Apr. 2017 vol. 25, 1 sup, pp. 180s-181s. Ab. No. 439. Meeting info: 24th Conf. retroviruses and opportunistic infections, Seattle WA, Feb. 13-16, 2017) (Year: 2017).*
Zaro ("Lipid-based carrier for prodrugs to enhance delivery," AAPS J. 2015, vol. 17, No. 1, pp. 83-92) (Year: 2015).*
Edgawa, B., et al., Long acting slow effective release antiretroviral therapy, Expert Opin Drug Deilv, 14(11): 1281-1291 (2017).
PCT/US2017/038693 International Search Report and Written Opinion dated Nov. 27, 2017.
PCT/US2019/057406 International Search Report and Written Opinion dated Jan. 16, 2020.
Sillman, B., et al., Creation of a long-acting nanoformulated dolutegravir, Nat Commun, 9(1): 443 (2018).
Zhou, T., et al., Creation of a nanoformulated cabotegravir prodrug with improved antiretroviral profiles, Biomaterials, 151: 53-65 (2018).
Zhou, T., Next generation of trasnslational long-acting cabotegravir, Electronic Theses and Dissertations University of Nebraska Medical Center, 139 pages (2018).
McMillan, J., et al., Pharmacokinetics of a long-acting nanoformulated dolutegravir prodrug in rhesus macaques, Antimicrob Agents Chemother, 62(1): e01316-e01317 (2018).
Gendelman, H.E., et al., The promise of long acting antiretroviral therapies: From need to manufacture, Trends Microbiol, 27(7): 593-606 (2019).
McMillan, J., et al., Pharmacokinetic testing of a first-generation cabotegravir prodrug in rhesus macaques, AIDS, 33(3): 585-588 (2019).
Application of Harold G. Petering and Harry H. Fall, Patent Appeal No. 6750, United States Court of Customs and Patent Appeals, Apr. 13, 1962.
U.S. Appl. No. 17/303,228 Office Action dated Aug. 11, 2021.
U.S. Appl. No. 17/303,229 Office Action dated Aug. 25, 2021.
Andrews, C.D., et al., A long-acting integrase inhibitor protects female macaques from repeated high-dose intravaginal SHIV challenge, Sci Transl Med, 7(270): 270ra4 (2015).
Andrews, C.D., et al., Long-Acting Integrase Inhibitor Protects Macaques from Intrarectal Simian/Human Immunodeficiency Virus, Science, 343(6175): 1151-1154 (2014).
Co-Pending U.S. Appl. No. 17/303,228, filed May 24, 2021.
Co-Pending U.S. Appl. No. 17/303,229, filed May 24, 2021.
Landovitz, R.J., et al., Safety, tolerability, and pharmacokinetics of long-acting injectable cabotegravir in low-risk HIV-uninfected individuals: HPTN 077, a phase 2a randomized controlled trial, PLoS Med, 15(11):e1002690 (2018).
Margolis, D.A., et al., Long-acting intramuscular cabotegravir and rilpivirine in adults with HIV-1 infection (LATTE-2): 96-week results of a randomised, open-label, phase 2b, non-inferiority trial, Lancet, 390(10101): 1499-1510 (2017).
Markowitz, M., et al., Safety and tolerability of long-acting cabotegravir injections in HIV-uninfected men (ECLAIR): a multicentre, double-blind, randomised, placebo-controlled, phase 2a trial, Lancet HIV, 4(8): e331-e340 (2017).
Radzio, J., et al., The long-acting integrase inhibitor GSK744 protects macaques from repeated intravaginal SHIV challenge, Sci Transl Med, 7(270): 270ra5 (2015).
Spreen, W., et al., GSK1265744 pharmacokinetics in plasma and tissue after single-dose long-acting injectable administration in healthy subjects, J Acquir Immune Defic Syndr, 67(5): 481-486 (2014).
Spreen, W.R., et al., Long-acting injectable antiretrovirals for HIV treatment and prevention, Curr Opin HIV AIDS, 8(6): 565-571 (2013).
Stellbrink, H-J, et al., Cabotegravir: its potential for antiretroviral therapy and preexposure prophylaxis, Curr Opin HIV AIDS, 13(4): 334-340 (2018).
Trezza. C., et al., Formulation and pharmacology of long-acting cabotegravir, Curr Opin HIV AIDS, 10(4): 239-245 (2015).

* cited by examiner

ANTIVIRAL PRODRUGS AND NANOFORMULATIONS THEREOF

CROSS-REFERENCE TO RELATED APPLICATIONS

This application is a continuation of International Application No. PCT/US2019/057406, filed Oct. 22, 2019, which claims priority under 35 U.S.C. § 119(e) to U.S. Provisional Patent Application No. 62/748,798, filed Oct. 22, 2018. The foregoing applications are incorporated by reference herein in their entireties.

STATEMENT AS TO FEDERALLY SPONSORED RESEARCH

This invention was made with government support under Grants Nos. R01 MH104147, P01 DA028555, R01 NS036126, P01 NS031492, R01 NS034239, P01 MH064570, P30 MH062261, P30 AI078498, R01 AG043540, and R56 AI138613 awarded by the National Institutes of Health. The government has certain rights in the invention.

FIELD OF THE INVENTION

The present invention relates generally to the delivery of therapeutics. More specifically, the present invention relates to compositions and methods for the delivery of therapeutic agents to a patient for the treatment of a disease or disorder.

BACKGROUND OF THE INVENTION

Remarkable progress has been made in the development of effective diagnostics and treatments against human immunodeficiency virus type one (HIV-1). Antiretroviral therapy (ART) has markedly reduced disease-associated morbidities and mortality, enabling a nearly normal quality of life for infected people (Vittinghoff, et al. (1999) J. Infect Dis., 179(3):717-720; Lewden, et al. (2007) J. Acquir. Immune Defic. Syndr., 46(1):72-77). However, ART requires lifelong treatment in order to suppress viral replication and prevent AIDS onset. Moreover, the effectiveness of ART can be hampered by HIV-1 resistance, drug toxicities, and poor patient adherence (Wensing, et al. (2014) Top. Antivir. Med., 22(3):642-650; Siliciano, et al. (2013) Curr. Opin. Virol., 3(5):487-494; Prosperi, et al. (2012) BMC Infect. Dis., 12:296-296; Van den Berk, et al. (2016) Abstract number: 948, In *Conference on Retroviruses and Opportunistic Infections*, 22-25; Siefried, et al. (2017) PLoS One 12(4): e0174613). Treatment fatigue, lack of financial and social support, co-existing mental symptoms, and/or substance abuse can result in the failure to adhere to critical ART regimens (Tucker, et al. (2017) EBioMedicine, 17:163-171).

Long-acting parenteral (LAP) antiretroviral drugs have improved regimen adherence (Spreen, et al. (2013) Curr. Opin. HIV AIDS, 8(6):565-571). Reducing the treatment schedule from daily to monthly or even less-frequent administration provides greater patient privacy and satisfaction and improves regimen adherence (Sangaramoorthy, et al. (2017) J. Assoc. Nurses AIDS Care, 28(4):518-531; Carrasco, et al. (2017) Afr. J. AIDS Res. 16(1):11-18; Williams, et al. (2013) Nanomed. Lond. 8(11):1807-1813). However, only a few antiretroviral drugs have been successfully reformulated into LAPs.

Cabotegravir (CAB) is an integrase inhibitor or integrase strand transfer inhibitor (INSTI) with low aqueous solubility, high melting point, high potency, long half-life, and slow metabolic clearance (Karmon, et al. (2015) J. Acquir. Immune Defic. Syndr., 68(3):39-41; Trezza, et al. (2015) Curr. Opin. HIV AIDS 10(4):239-245). These properties enable CAB to be formulated in a 200-mg/mL suspension (CAB LAP) and administered intramuscularly monthly or even less frequently (Margolis, et al. (2017) Lancet 390 (10101):1499-1510; Spreen, W. W. (2014) J. Acquir. Immune Defic. Syndr., 67(5):481-486). Notably, CAB plus rilpivirine (RPV) is the first long-acting combination ART regimen where monthly or every other month CAB and RPV LAP formulations have demonstrated comparable antiretroviral activity to daily oral three-drug combinations for maintenance therapy (Margolis, et al. (2017) Lancet 390 (10101):1499-1510).

Advantageously, CAB is primarily metabolized by uridine diphosphate glucuronosyltransferase (UGT) 1A1 and has a low potential to interact with other antiretroviral drugs (Trezza, et al. (2015) Curr. Opin. HIV AIDS 10(4):239-245; Bowers, et al. (2016) Xenobiotica 46(2):147-162). CAB LAP is highly protective against rectal, vaginal, and intravenous simian/human immunodeficiency virus (SHIV) transmission in non-human primates and has been advanced into clinical trials for HIV prevention (NCT02720094) (Andrews, et al. (2014) Science 343(6175):1151-1154; Andrews, et al. (2015) Sci. Transl. Med., 7(270) 270ra4; Radzio, et al. (2015) Sci. Transl. Med., 7(270) 270ra5-270ra5; Andrews, et al. (2016) AIDS 2016:461-467). However, the dosing pattern of CAB LAP has limitations. Specifically, split injections given in 2 mL volumes are required which leads to treatment cessations because of intolerable injection site reactions (Margolis, et al. (2017) Lancet 390 (10101):1499-510; Markowitz, et al. (2017) Lancet HIV 4(8):331-340). Moreover, the maximal dosing interval is only 8 weeks. Recently, the administration of CAB LAP every 12 weeks has been tested with the aim of maintaining plasma CAB concentrations above 4 times protein-binding-adjusted 90% inhibitory concentration (4×PA-$IC_{90}$, 660 ng/mL), a concentration demonstrated to be protective against new infections in macaques (Spreen, W. W. (2014) J. Acquir. Immune Defic. Syndr., 67(5):481-486; Andrews, et al. (2014) Science 343(6175):1151-1154; Andrews, et al. (2015) Sci. Transl. Med., 7(270) 270ra4; Radzio, et al. (2015) Sci. Transl. Med., 7(270) 270ra5-270ra5; Andrews, et al. (2016) AIDS 2016:461-467; Markowitz, et al. (2017) Lancet HIV 4(8):331-340; Spreen, et al. (2014) J. Acquir. Immune Defic. Syndr., 67(5):487-492). However, two-thirds of participants had faster than anticipated drug absorption leading to plasma drug concentrations below the targeted effective concentration of 4×PA-$IC_{90}$ at 12 weeks. Thus, ways to extend the dose interval beyond 8 weeks and reduce injection volumes to improve regimen adherence are greatly needed (Boyd, et al. (2017) Lancet 390(10101):1468-1470).

SUMMARY OF THE INVENTION

In accordance with the instant invention, prodrugs of integrase inhibitors are provided. In a particular embodiment, the prodrug comprises an integrase inhibitor modified with an ester comprising an aliphatic or alkyl group (e.g., an aliphatic or alkyl comprising about 3 to about 30 carbons). In a particular embodiment, the aliphatic or alkyl group is the alkyl chain of a fatty acid or a saturated linear aliphatic chain, optionally substituted with at least one heteroatom. In a particular embodiment, the integrase inhibitor is selected from the group consisting of cabotegravir (CAB), raltegravir (RAL), elvitegravir (EVG), dolutegravir (DTG), and bictegravir (BIC). Compositions comprising at least one prodrug of the instant invention and at least one pharmaceutically acceptable carrier are also encompassed by the present invention.

In accordance with another aspect of the instant invention, nanoparticles comprising at least one prodrug of the instant invention and at least one polymer or surfactant are provided. In a particular embodiment, the prodrug is crystalline. In a particular embodiment, the polymer or surfactant is an amphiphilic block copolymer such as an amphiphilic block copolymer comprising at least one block of poly(oxyethylene) and at least one block of poly(oxypropylene) (e.g., poloxamer 407). The nanoparticle may comprise a polymer or surfactant linked to at least one targeting ligand. An individual nanoparticle may comprise targeted and non-targeted surfactants. In a particular embodiment, the nanoparticles have a diameter of about 100 nm to 1 Compositions comprising at least one nanoparticle of the instant invention and at least one pharmaceutically acceptable carrier are also encompassed by the present invention.

In accordance with another aspect of the instant invention, methods for treating, inhibiting, and/or preventing a disease or disorder in a subject in need thereof are provided. The methods comprise administering to the subject at least one prodrug or nanoparticle of the instant invention, optionally within a composition comprising a pharmaceutically acceptable carrier. In a particular embodiment, the disease or disorder is a viral infection (e.g., a retroviral infection). In a particular embodiment, the method further comprises administering at least one further therapeutic agent or therapy for the disease or disorder, e.g., at least one additional anti-HIV compound.

BRIEF DESCRIPTIONS OF THE DRAWING

Figure 1B:
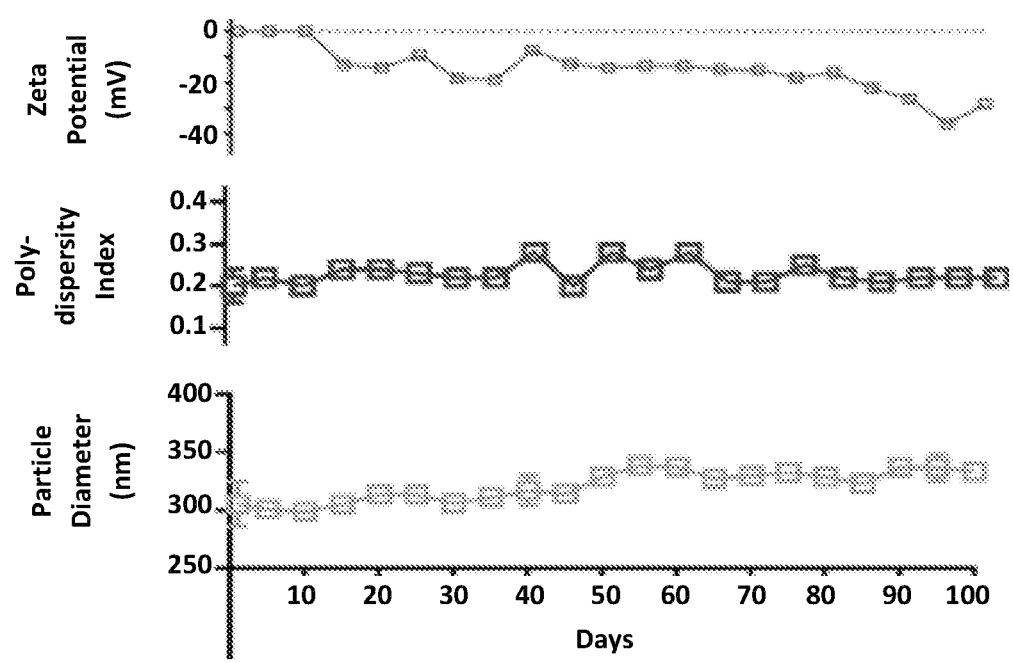
Figure 2A:
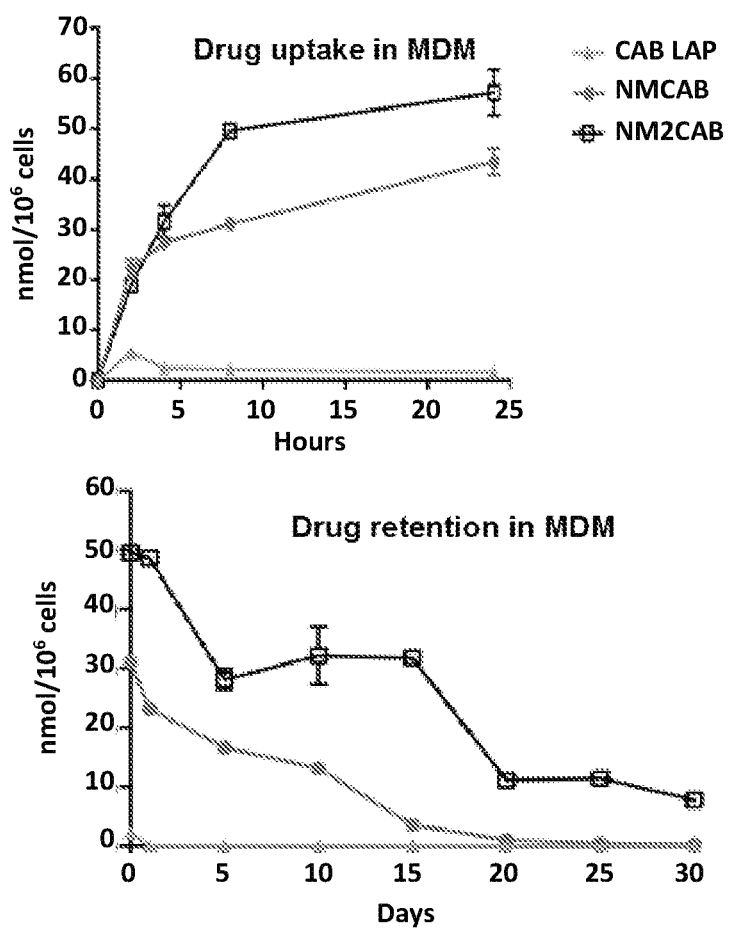
Figure 2B:
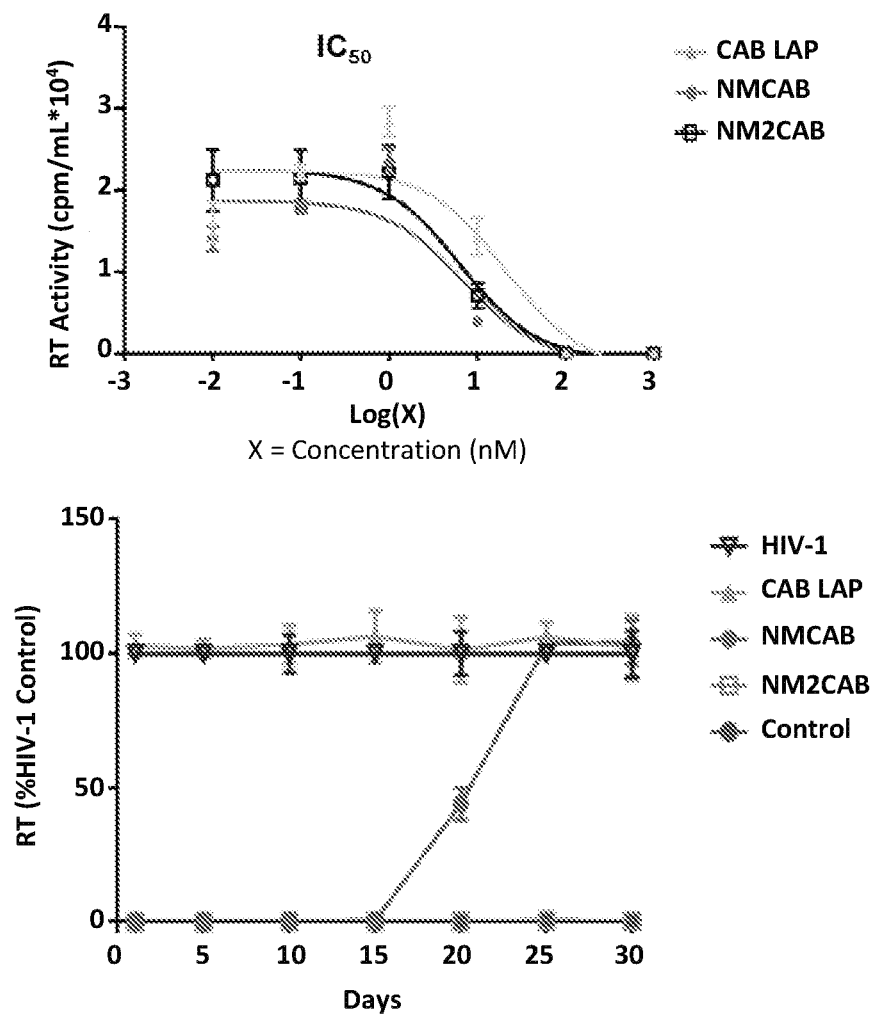
Figure 2C:
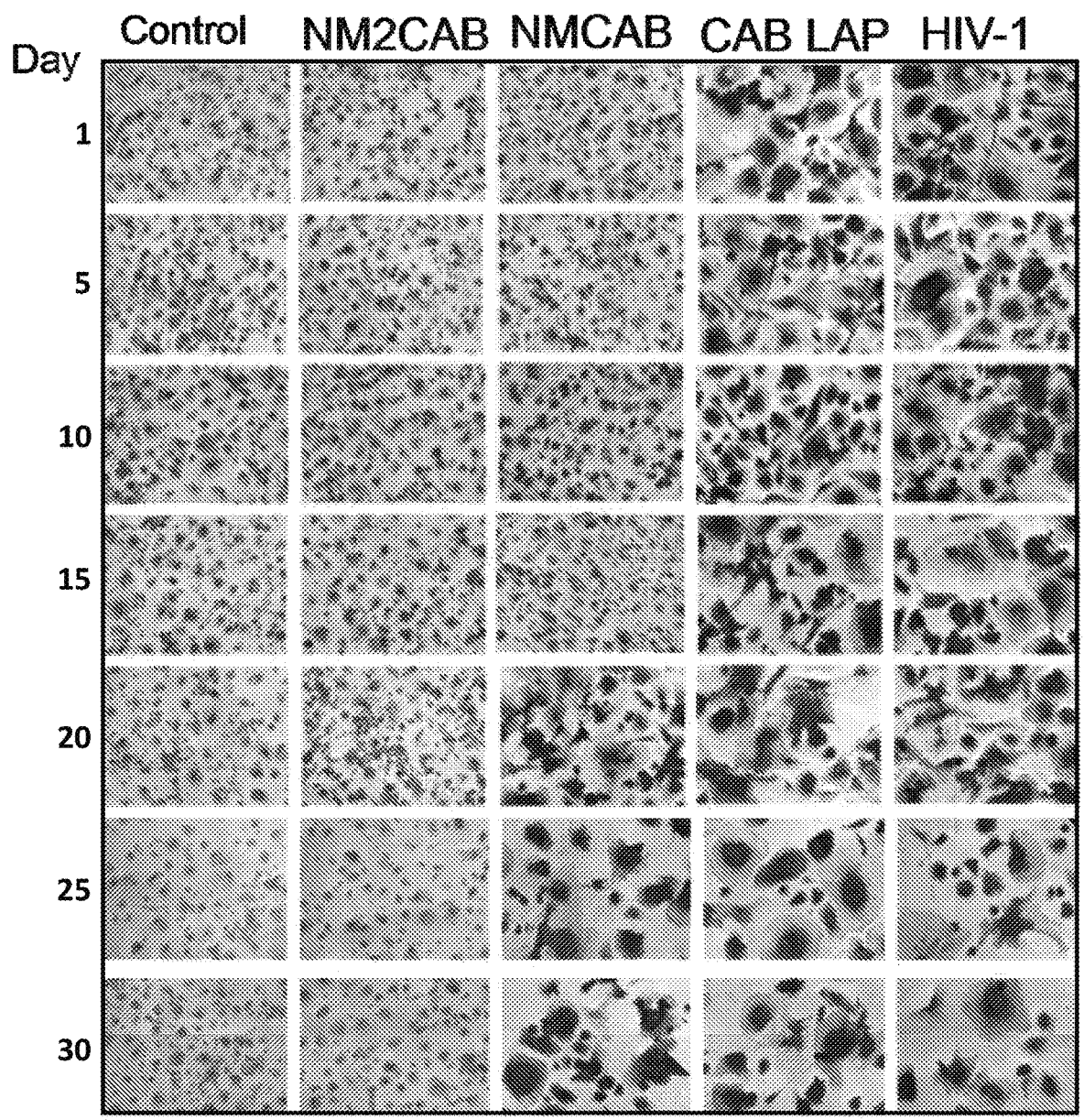

FIG. 1A provides images of NM2CAB (top) and NCAB (bottom) nanoparticles as determined by scanning electron microscopy. FIG. 1B provides graphs of NM2CAB nanoparticle stability at 25° C. over the indicated periods of time. Particularly, nanoparticle zeta potential (top), polydispersity index (middle), and particle diameter (bottom) were determined by dynamic light scattering FIG. 2A provides a graph (top) of the drug uptake as measured by UPLC-UV/Vis by human monocyte derived macrophages (MDM) and a graph (bottom) of drug retention by MDM and collected at the indicated timepoints for intracellular drug analysis. FIG. 2B provides a graph (top) of HIV-1 reverse transcriptase activity at the indicated concentration of drug and a graph (bottom) of HIV-1 reverse transcriptase activity in MDM treated with drug and challenged with HIV-1ADA and measured at the indicated timepoints post-treatment. FIG. 2C provides images of p24 stained MDM cells post-challenge.

Figure 3A:
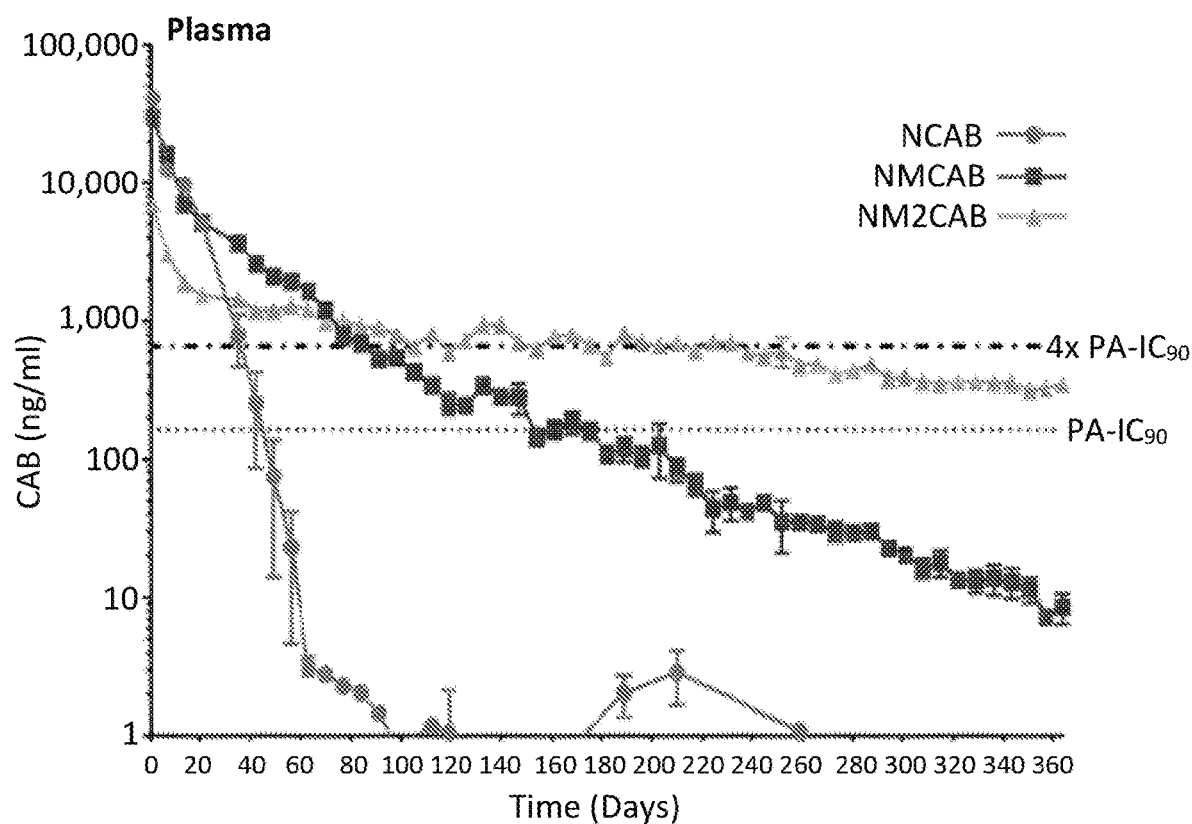
Figure 3B:
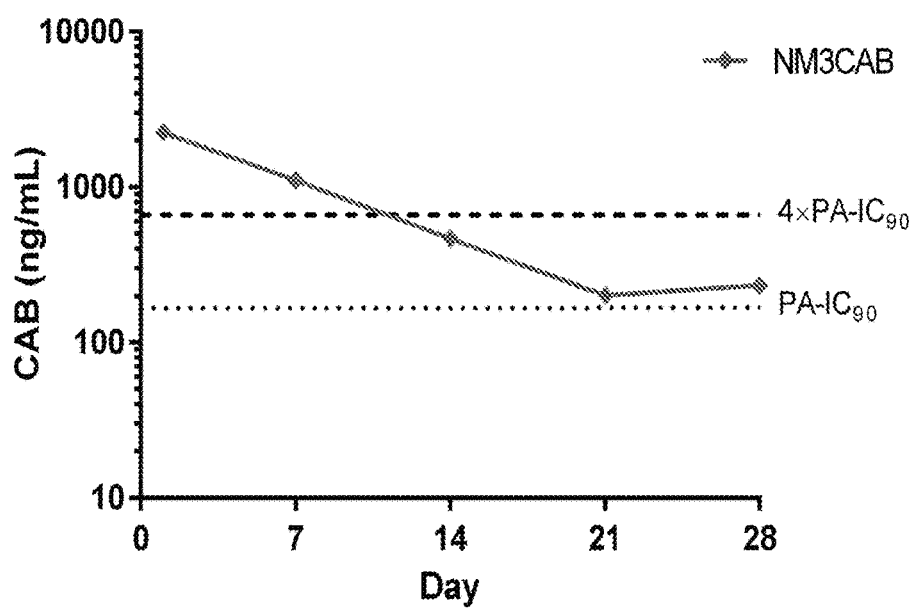

FIG. 3A provides a graph of plasma CAB levels after a single intramuscular (IM) dose of NCAB, NMCAB or NM2CAB in female NSG (NOD scid gamma mouse) mice. Administered dose was 45 mg CAB equivalents (eq)/kg. Top bold dashed line indicates plasma CAB 4×PA-$IC_{90}$ of 664 ng/ml and the bottom stippled line shows the plasma CAB 1×PA-$IC_{90}$ of 166 ng/ml. FIG. 3B provides a graph of plasma CAB levels after a single intramuscular (IM) dose of NM3CAB in female NSG (NOD scid gamma mouse) mice. Administered dose was 45 mg CAB equivalents (eq)/kg. Top bold dashed line indicates plasma CAB 4×PA-$IC_{90}$ of 664 ng/ml and the bottom stippled line shows the plasma CAB 1×PA-$IC_{90}$ of 166 ng/ml.

Figure 4:
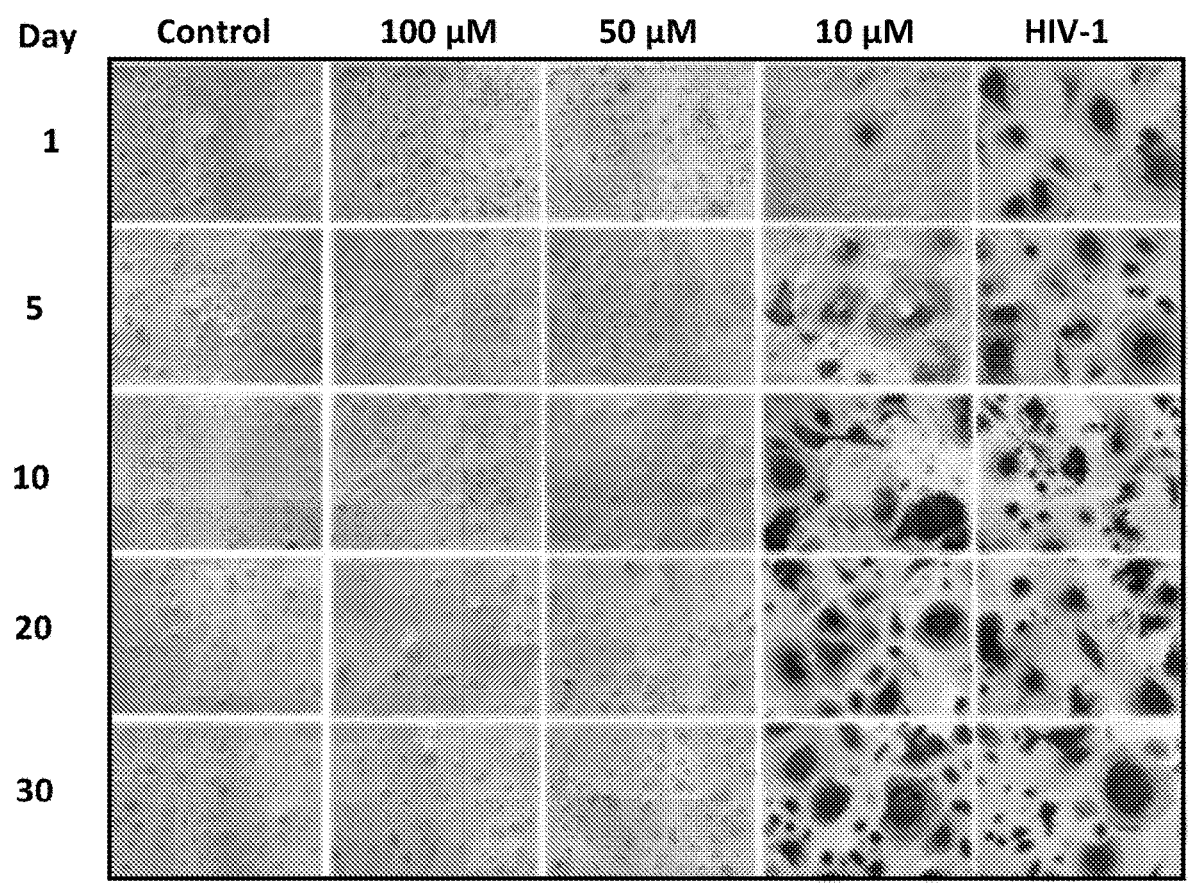

FIG. 4 provides images of the antiretroviral dose-response of NM2CAB at 10, 50 or 100 μM concentration by immunocytochemistry for HIV-1 p24 antigen.

Figure 5:
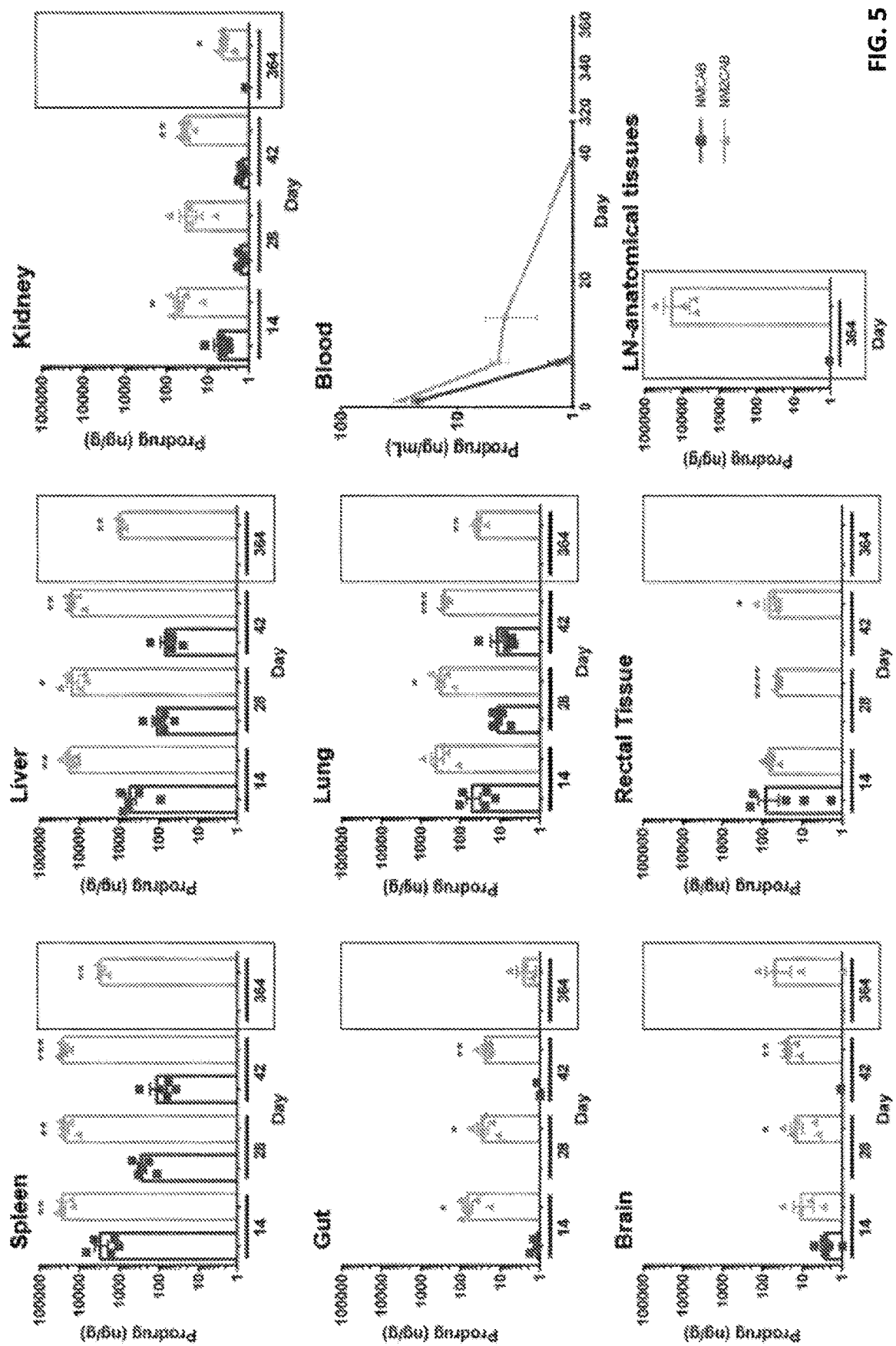

FIG. 5 provides graphs of prodrug levels. The tissue and blood biodistribution of prodrugs (MCAB or M2CAB) were assessed at 14, 28, 42 and 364 days after a single IM injection of NMCAB or NM2CAB. Prodrug levels were measured in the spleen, liver, gut, lung, brain, rectal tissue, kidneys, lymph nodes-anatomical associated tissues and blood. Prodrug levels were determined by LC-MS/MS. Data are expressed as mean±SEM. For day 14, 28 and 42 groups, animal numbers in each group were N=5, and for day 364 group, animal numbers were N=3 (NMCAB), N=4 (NM2CAB). A one-way ANOVA followed by a Tukey post's test was used to compare drug levels in tissues among three treatments (*$P<0.05$, $P<0.01$, *$P<0.001$).

Figure 6A:
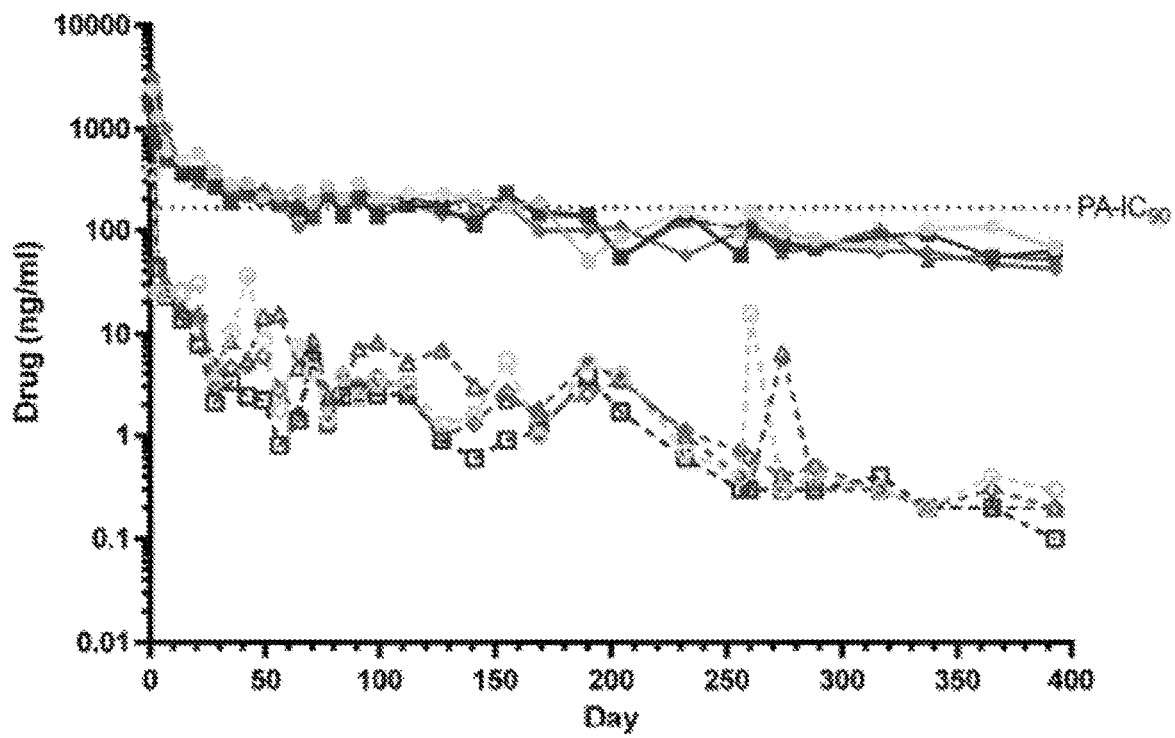
Figure 6B:
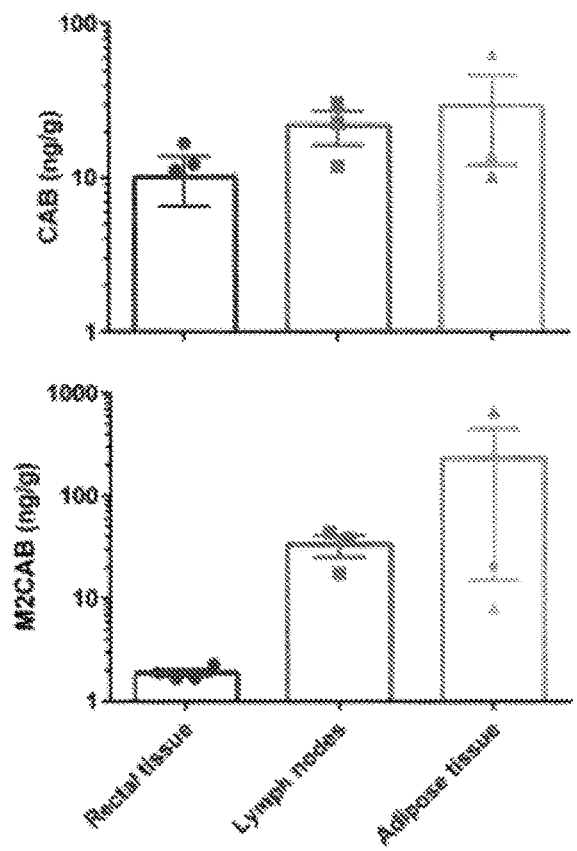

FIGS. 6A and 6B provide graphs of the pharmacokinetics and biodistribution of NM2CAB in rhesus macaques. Four rhesus macaques were administered with 45 mg/kg CAB-equivalent dose of NM2CAB by a single IM injection. Plasma samples were collected and assayed for CAB (top lines) and M2CAB (bottom lines) levels up to day 393 (FIG. 6A). Rectal, lymph node, and adipose tissue biopsies were collected at day 204 following drug administration and assayed for both CAB (top) and M2CAB (bottom) concentrations (FIG. 6B). Both plasma and tissue drug concentrations were determined by LCMS/MS.

DETAILED DESCRIPTION OF THE INVENTION

Maximal restriction of viral load in tissue infectious sites can facilitate viral eradication strategies. This can be achieved by generation of potent lipophilic and hydrophobic antiretroviral prodrug nanocrystals stabilized by surfactants. Hydrophobicities, drug hydrolysis rates, and antiretroviral potencies must be balanced for optimal therapeutic effect. Herein, it is demonstrated that the manipulation of the size of the hydrophobic and lipophilic carbon chain length of a prodrug can optimize therapeutic efficacy, particularly with regard to long acting slow effective release antiretroviral therapy (LASER ART). LASER ART refers to a long acting antiretroviral drug generated from a nanocrystal prodrug with a lipid tail. Myristoylated CAB prodrug nanocrystal provide sustained plasma CAB concentrations at the PA-$IC_{90}$ for 4 months in rhesus macaques after single 45 mg/kg CAB equivalent intramuscular injection dose. Herein, it is shown that further chemical modifications unexpectedly serve to enhance CAB lipophilicity and hydrophobicity, improve drug potency, and slow prodrug hydrolysis, thereby extensively extending the half-life of the parent drug. The novel cabotegravir prodrugs (M2CAB) enhance drug encapsulation with appropriate excipients and stabilizers, such as poloxamer 407 (P407). M2CAB nanoformulations (NM2CAB) provide sustained drug release and site specific antiretroviral drug delivery. The prodrugs comprise native drug conjugated to hydrophobic moieties via hydrolyzable covalent bonds. The NM2CAB nanoformulations were readily taken up by human monocyte-derived macrophages (MDM) with sustained drug retention for 30 days in vitro; whereas parent drug nanoformulation (NCAB) or first generation myristoylated cabotegravir (NMCAB) showed HIV-1 breakthrough in MDM within one or 20 days of treatment, respectively. Notably, MDM treated with NM2CAB exhibited sustained antiretroviral activities following HIV-1 challenge for up to 30 days after single drug treatment. HIV-1p24 was not detected in the NM2CAB treated group at 5 day incremental time points for up to or greater than 30 days. Further, a single intramuscular (IM) injection of NM2CAB at 45 mg CAB equivalents/kg into female NSG (NOD scid gamma mouse) mice demonstrated a zero order controlled release kinetics of active CAB and provided drug levels at or above 4 times the PA-IC$_{90}$ for greater than 5 months. The NM2CAB nanoformulations presented herein improves upon current combination ART regimens that require multiple daily administrations by reducing pill burden, lowering the risk of viral rebound, limiting toxicities, and/or allowing for drug penetration into viral reservoirs. Importantly, NM2CAB also facilitates a dosing interval of once every six months (or even less frequently) to maximize the effectiveness of pre-exposure prophylaxis or treatment regimens.

Long acting slow effective release ART (LASER ART) formulations can extend dosing intervals, reduce systemic toxicity, and improve pharmacokinetic (PK) and pharmacodynamic (PD) profiles (Sillman, et al., Nat. Commun. (2018) 9:443; Zhou, et al., Biomaterials (2018) 151:53-65; McMillan, et al., Antimicrob. Agents Chemother. (2018) 62:e01316-17). Herein, novel integrase inhibitor prodrugs, long-acting slow effective release formulations thereof, and methods of synthesis and use thereof are provided. Integrase inhibitors (integrase strand transfer inhibitors (INSTIs)) are a class of antiretroviral drug designed to block the action of integrase (e.g., HIV integrase), a viral enzyme that inserts the viral genome into the DNA of the host cell. Examples of integrase inhibitors include, without limitation, cabotegravir (CAB, GSK1265744), raltegravir (RAL), elvitegravir (EVG), dolutegravir (DTG, GSK1349572), bictegravir (BIC, GS-9883), BI 224436 (Boehringer Ingelheim, Ingelheim, Germany), and MK-2048 (Merck, Kenilworth, N.J.). The hydrophobic and lipophilic prodrugs and their slow effective release formulations exhibit enhanced potency and efficacy, increased cellular and tissue penetration and extended half-lives compared to parent integrase inhibitor. The prodrugs and their formulations of the instant invention and their combinations can be used in the management of viral (e.g., retroviral) infections.

Treatments of viral infections, particularly HIV infections, which are currently available, include inhibitors of viral entry, nucleoside reverse transcriptase, nucleotide reverse transcriptase, integrase, and protease. Resistance is linked to a shortened drug half-life, the viral life cycle, and rapid mutations resulting in a high genetic variability. Combination therapies, e.g., antiretroviral therapies (ART), which are considered "cocktail" therapy, have gained substantial attention. Benefits include decreased viral resistance, limited toxicities, improved adherence to therapeutic regimens and sustained antiretroviral efficacy. Combination therapies minimize potential drug resistance by suppressing viral (e.g., HIV) replication, thereby reducing spontaneous resistant mutants. Treatment failure is attributed, in part, to the short drug half-lives. Furthermore, failure can also be attributed, in part, to limited drug access to tissue and cellular viral reservoirs, thereby precluding viral eradication efforts. To these ends, the development of cell and tissue targeted nanoformulated prodrug (nanoparticle) platforms are of considerable interest in the management of viral (e.g., HIV) infections. Pre-exposure prophylaxis (PrEP) is another strategy used in the management of viral (e.g., HIV) transmission. For example, TRUVADA® (tenofovir/emtricitabine) has been approved for pre-exposure prophylaxis against HIV infection. Additionally, the combination of lamivudine and zidovudine (COMBIVIR®) has been used as pre-exposure prophylaxis and post-exposure prophylaxis.

The prodrugs and nanoformulated prodrugs (nanoparticles) provided herein unexpectedly extend the drug half-life, increase hydrophobicity and lipophilicity, and improve antiretroviral efficacy. This will benefit people who have to receive daily high doses or even several doses a day, since lower dosage with less dosing frequency would not only decrease the side effects, but also be convenient to the patients. The prodrugs and nanoformulated prodrugs (nanoparticles) provided herein may also be used as a post-exposure treatment and/or pre-exposure prophylaxis (e.g., for people who are at high risk of contracting HIV-1). In other words, the prodrugs and nanoparticles of the instant invention and their combination may be used to prevent a viral infection (e.g., HIV infection) and/or treat or inhibit an acute or long term viral infection (e.g., HIV infection). While the prodrugs and nanoparticles of the instant invention are generally described as anti-HIV agents, the prodrugs and nanoformulations of the instant invention are also effective against other viral infections including, without limitation: retroviruses (e.g., lentiviruses), hepatitis B virus (HBV), hepatitis C virus (HCV), and human T-cell leukemia viruses (HTLV), particularly retroviruses.

The present invention describes novel, potent, broad spectrum prodrugs with improved biological activity over parent drugs. Methods for the encapsulation of the prodrugs into long acting slow effective formulations for efficient intracellular and tissue delivery and extended drug half-lives are also provided. The long acting slow effective release (LASER) compositions described herein exhibit enhanced potency and may be used as effective therapeutic or preventative interventions against viral infections (e.g., retroviral infections).

Prodrugs of the instant invention allow for the efficient intracellular delivery of integrase inhibitors. Herein, prodrugs are provided which are derivatives of integrase inhibitors wherein a chemical moiety, particularly an oxygen containing moiety such as a hydroxyl group, has been replaced with an ester moiety comprising a hydrophobic and lipophilic cleavable moiety (e.g., therapeutic fatty alcohols). The hydrophobic and lipophilic cleavable moiety (e.g., therapeutic fatty alcohols) can exhibit antiviral activity against enveloped viruses (Katz, et al., Ann. NY Acad. Sci. (1994) 724:472-88). Notably, synergistic interactions between therapeutic fatty alcohols and nucleoside analogs can substantially enhance antiviral potency of the nucleosides (Marcelletti, et al., Antiviral Res. (2002) 56:153-66).

As described herein, the prodrugs may comprise labile therapeutic fatty alcohols to improve drug potency, accelerate intracellular and tissue penetrance, protein binding, and bioavailability. The hydrophobic nature of the synthesized prodrugs facilitates encapsulation into long acting slow release drug nanocrystals with improved biopharmaceutical features. The nanoformulations of the instant invention may be composed of prodrug particles dispersed in sterile aqueous suspensions and stabilized by polymeric excipients, lipids, and/or surfactants or polymers. Without being bound by theory, the mechanism of drug release involves dissolution of the prodrug from the nanoparticle followed by efficient cleavage to generate two bioactive agents, i.e., the integrase inhibitor and the broad-spectrum antiviral fatty alcohols.

The benefits of the system described herein include, without limitation, improved drug potency, bioavailability and extended half-life for patient convenience. Indeed, the nanoformulations described in this invention displayed significant increase in drug uptake by monocyte-derived macrophages (MDM). Also, the modified drug and nanoparticles exhibited enhanced potency through increased and extended inhibition of viral replication. Therefore, the nanoformulations of the instant invention allow for enhancement of antiviral potency and accelerated drug delivery to anatomical reservoirs of infection.

In accordance with the instant invention, prodrugs of integrase inhibitors are provided. In a particular embodiment, the prodrug comprises an integrase inhibitor wherein a chemical moiety such as a hydroxyl group is replaced with an ester comprising an optionally substituted aliphatic or alkyl group. In a particular embodiment, the ester comprises a hydrocarbon chain, particularly a hydrocarbon chain of 16-20 carbon atoms in length or 18 carbon atoms in length (numbering here is inclusive of the carbon in the C=O of the ester).

In a particular embodiment, the integrase inhibitor is selected from the group consisting of cabotegravir (CAB), raltegravir (RAL), elvitegravir (EVG), dolutegravir (DTG), bictegravir (BIC), BI 224436, and MK-2048. In a particular embodiment, the integrase inhibitor is selected from the group consisting of cabotegravir (CAB), raltegravir (RAL), elvitegravir (EVG), dolutegravir (DTG), and bictegravir (BIC). Examples of the chemical structures of these integrase inhibitors are:

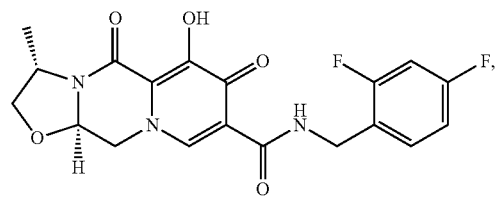

cabotegravir (CAB)

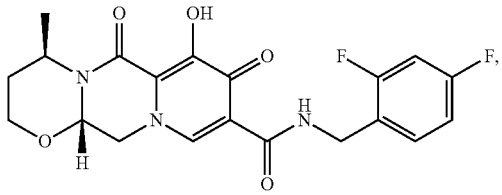

dolutegravir (DTG)

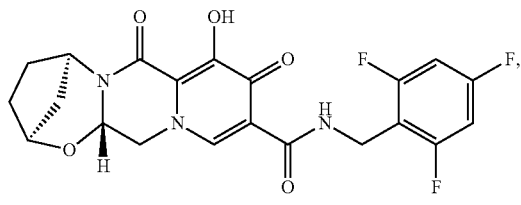

bictegravir (BIC)

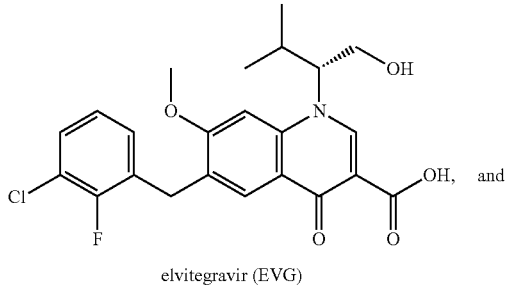

elvitegravir (EVG)

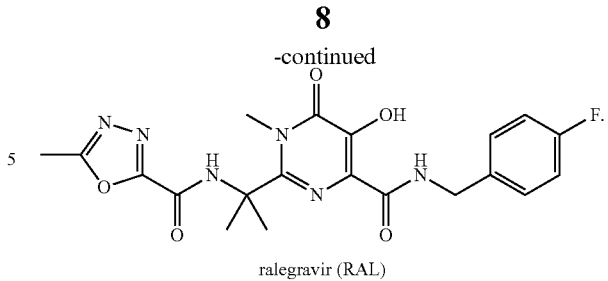

raltegravir (RAL)

In a particular embodiment, the prodrug of the instant invention is selected from the following group or a pharmaceutically acceptable salt thereof:

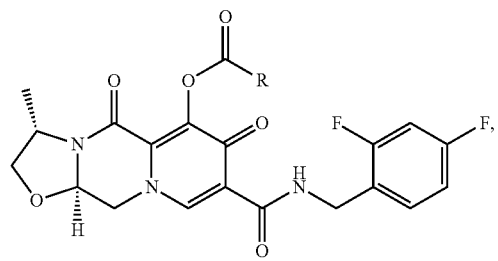

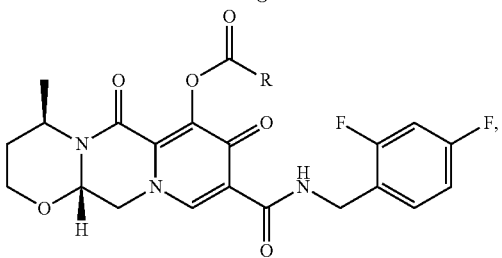

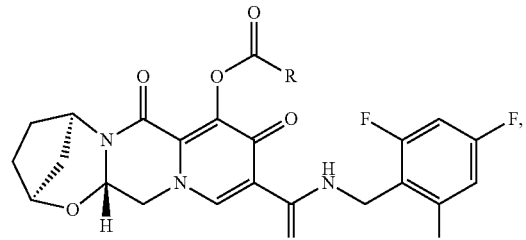

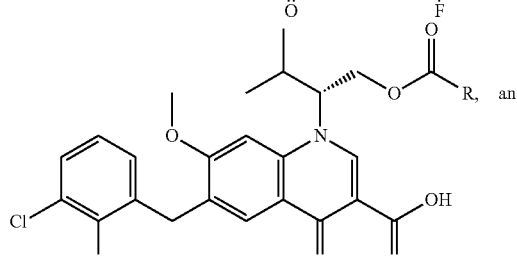

, and

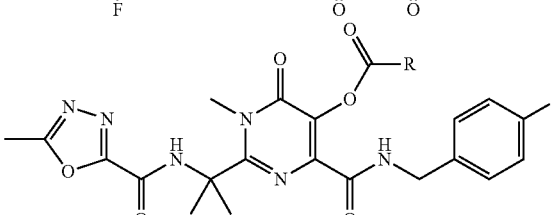

wherein R is an optionally substituted aliphatic or alkyl. The aliphatic or alkyl group may be unsaturated or saturated, and may be substituted with at least one heteroatom (e.g., O, N, or S). In a particular embodiment, R may contain an aromatic moiety that may be substituted with at least one heteroatom (e.g., O, N, or S).

In a particular embodiment, the alkyl or aliphatic group is hydrophobic. In a particular embodiment, R is an optionally substituted hydrocarbon chain, particularly saturated. In a particular embodiment, R is a saturated linear aliphatic chain. In a particular embodiment, the alkyl or aliphatic group comprises about 3 to about 30 carbons (e.g., in the main chain of the alkyl or aliphatic group), which may be substituted with at least one heteroatom (e.g., O, N, or S). In a particular embodiment, R is a C14-C21 unsaturated or saturated alkyl or aliphatic group, which may be substituted with at least one heteroatom (e.g., O, N, or S). In a particular embodiment, R is a C14-C19 unsaturated or saturated alkyl or aliphatic group, which may be substituted with at least one heteroatom (e.g., O, N, or S). In a particular embodiment, R is a C14-C17 unsaturated or saturated alkyl or aliphatic group, which may be substituted with at least one heteroatom (e.g., O, N, or S). In a particular embodiment, R is a C15-C21 unsaturated or saturated alkyl or aliphatic group, which may be substituted with at least one heteroatom (e.g., O, N, or S). In a particular embodiment, R is a C15-C19 unsaturated or saturated alkyl or aliphatic group, which may be substituted with at least one heteroatom (e.g., O, N, or S). In a particular embodiment, R is a C15-C17 unsaturated or saturated alkyl or aliphatic group, which may be substituted with at least one heteroatom (e.g., O, N, or S). In a particular embodiment, R is a C16-C21 unsaturated or saturated alkyl or aliphatic group, which may be substituted with at least one heteroatom (e.g., O, N, or S). In a particular embodiment, R is a C16-C19 unsaturated or saturated alkyl or aliphatic group, which may be substituted with at least one heteroatom (e.g., O, N, or S). In a particular embodiment, R is a C17-C21 unsaturated or saturated alkyl or aliphatic group, which may be substituted with at least one heteroatom (e.g., O, N, or S). In a particular embodiment, R is a C17-C19 unsaturated or saturated alkyl or aliphatic group, which may be substituted with at least one heteroatom (e.g., O, N, or S). In a particular embodiment, R is a C17 unsaturated or saturated alkyl or aliphatic group, which may be substituted with at least one heteroatom (e.g., O, N, or S).

In a particular embodiment, R is the alkyl chain of a fatty acid (saturated or unsaturated), particularly a C16-C22 fatty acid, a C16-C20 fatty acid, a C16-C18 fatty acid, a C18-C22 fatty acid, a C18-C20 fatty acid, or a C18 fatty acid (numbering here is inclusive of the carbon in the C=O of the ester).

In a particular embodiment, R is a saturated linear aliphatic chain or a hydrocarbon chain of at least 14 carbons (e.g., 14 to 21 carbons in length in the chain, 14 to 19 carbons in length in the chain, 14 to 17 carbons in length in the chain, 15 to 21 carbons in length in the chain, 15 to 19 carbons in length in the chain, 15 to 17 carbons in length in the chain, or 17 carbons in length in the chain). In a particular embodiment, R is a saturated linear aliphatic chain or a hydrocarbon chain of 14, 15, 16, 17, 18, 19, 20, or 21 carbons in length, particularly 14, 15, 16, 17, 18, or 19 carbons in length, 15, 16, or 17 carbons in length, or 17 carbons in length. In a particular embodiment, R is a saturated linear aliphatic chain or a hydrocarbon chain of 17 carbons in length.

In a particular embodiment, the prodrug of the instant invention is:

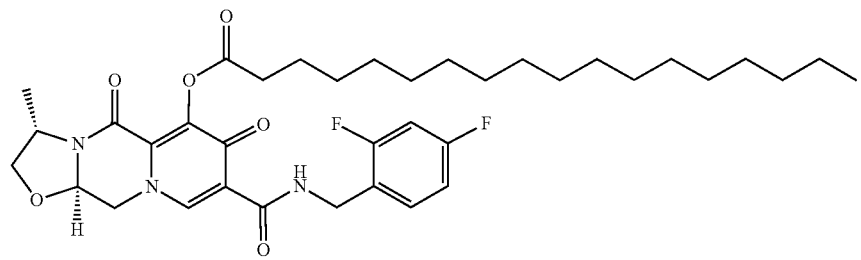 [SMILES: CCCCCCCCCCCCCCCCCC(=O)Oc1c2n(cc(C(=O)NCc3ccc(F)cc3F)c1=O)C[C@H]1OC[C@H](C)N1C2=O]

(M2CAB) or a pharmaceutically acceptable salt thereof.

The instant invention also encompasses nanoparticles (sometimes referred to herein as nanoformulations) comprising the prodrug of the instant invention. The nanoparticles may be used for the delivery of the compounds to a cell or host (e.g., in vitro or in vivo). In a particular embodiment, the nanoparticle is used for the delivery of antiretroviral therapy to a subject. The nanoparticles of the instant invention comprise at least one prodrug and at least one surfactant or polymer. In a particular embodiment, the nanoparticles comprise a spectroscopic-defined surfactant/polymer:drug ratio that maintains optimal targeting of the drug nanoparticle to maintain a macrophage depot. These components of the nanoparticle, along with other optional components, are described hereinbelow.

Methods of synthesizing the nanoparticles of the instant invention are known in the art. In a particular embodiment, the methods generate nanoparticles comprising a prodrug (e.g., crystalline or amorphous) coated (either partially or completely) with a polymer and/or surfactant. Examples of synthesis methods include, without limitation, milling (e.g., wet milling), homogenization (e.g., high pressure homogenization), particle replication in nonwetting template (PRINT) technology, and/or sonication techniques. For example, U.S. Patent Application Publication No. 2013/0236553, incorporated by reference herein, provides methods suitable for synthesizing nanoparticles of the instant invention. In a particular embodiment, the polymers or surfactants are firstly chemically modified with targeting ligands and then used directly or mixed with non-targeted polymers or surfactants in certain molar ratios to coat on the surface of prodrug suspensions—e.g., by using a nanoparticle synthesis process (e.g., a crystalline nanoparticle synthesis process) such as milling (e.g., wet milling), homogenization (e.g., high pressure homogenization), particle replication in nonwetting template (PRINT) technology, and/or sonication techniques, thereby preparing targeted nanoformulations. The nanoparticles may be used with or without further purification, although the avoidance of further purification is desirable for quicker production of the nanoparticles. In a particular embodiment, the nanoparticles are synthesized using milling and/or homogenization. Targeted nanoparticles (e.g., using ligands (optionally with high molecular weight)) may be developed through either physically or chemically coating and/or binding on the surface of polymers or surfactants and/or drug nanosuspensions.

In a particular embodiment, the nanoparticles of the instant invention are synthesized by adding the prodrug (e.g., crystals) to a polymer or surfactant solution and then generating the nanoparticles (e.g., by wet milling or high pressure homogenization). The prodrug and polymer or surfactant solution may be agitated prior the wet milling or high pressure homogenization.

The nanoparticles of the instant invention may be used to deliver at least one prodrug of the instant invention to a cell or a subject (including non-human animals). The nanoparticles of the instant invention may further comprise at least one other agent or compound, particularly a bioactive agent, particularly a therapeutic agent (e.g., antiviral compound) or diagnostic agent, particularly at least one antiviral or anti-retroviral. In a particular embodiment, the nanoparticles of the instant invention comprise at least two therapeutic agents, particularly wherein at least one is a prodrug of the instant invention. For example, the nanoparticle may comprise an integrase inhibitor prodrug of the instant invention and at least one other therapeutic agent (e.g., an anti-HIV agent).

In a particular embodiment, the nanoparticles of the instant invention are a submicron colloidal dispersion of nanosized prodrug crystals stabilized by polymers or surfactants (e.g., surfactant-coated drug crystals; a nanoformulation). In a particular embodiment, the prodrug may be crystalline (solids having the characteristics of crystals), amorphous, or are solid-state nanoparticles of the prodrug that is formed as crystal that combines the drug and polymer or surfactant. In a particular embodiment, the prodrug is crystalline. As used herein, the term "crystalline" refers to an ordered state (i.e., non-amorphous) and/or a substance exhibiting long-range order in three dimensions. In a particular embodiment, the majority (e.g., at least 50%, 60%, 70%, 80%, 90%, 95% or more) of the prodrug and, optionally, the hydrophobic portion of the surfactant are crystalline.

In a particular embodiment, the nanoparticle of the instant invention is up to about 2 or 3 µm in diameter (e.g., z-average diameter) or its longest dimension, particularly up to about 1 µm (e.g., about 100 nm to about 1 µm). For example, the diameter or longest dimension of the nanoparticle may be about 50 to about 800 nm. In a particular embodiment, the diameter or longest dimension of the nanoparticle is about 50 to about 750 nm, about 50 to about 500 nm, about 200 nm to about 500 nm, about 200 nm to about 400 nm, or about 250 nm to about 350 nm. The nanoparticles may be, for example, rod shaped, elongated rods, irregular, or round shaped. The nanoparticles of the instant invention may be neutral or charged. The nanoparticles may be charged positively or negatively.

As stated hereinabove, the nanoparticles of the instant invention comprise at least one polymer or surfactant. A "surfactant" refers to a surface-active agent, including substances commonly referred to as wetting agents, detergents, dispersing agents, or emulsifying agents. Surfactants are usually organic compounds that are amphiphilic.

Examples of polymers or surfactants include, without limitation, synthetic or natural phospholipids, PEGylated lipids (e.g., PEGylated phospholipid), lipid derivatives, polysorbates, amphiphilic copolymers, amphiphilic block copolymers, poly(ethylene glycol)-co-poly(lactide-co-glycolide) (PEG-PLGA), their derivatives, ligand-conjugated derivatives and combinations thereof. Other polymers or surfactants and their combinations that can form stable nanosuspensions and/or can chemically/physically bind to the targeting ligands of HIV infectable/infected CD4+ T cells, macrophages and dendritic cells can be used in the instant invention. Further examples of polymers or surfactants include, without limitation: 1) nonionic surfactants (e.g., pegylated and/or polysaccharide-conjugated polyesters and other hydrophobic polymeric blocks such as poly (lactide-co-glycolide) (PLGA), polylactic acid (PLA), polycaprolactone (PCL), other polyesters, poly(propylene oxide), poly(1,2-butylene oxide), poly(n-butylene oxide), poly(tetrahydrofurane), and poly(styrene); glyceryl esters, polyoxyethylene fatty alcohol ethers, polyoxyethylene sorbitan fatty acid esters, polyoxyethylene fatty acid esters, sorbitan esters, glycerol monostearate, polyethylene glycols, polypropyleneglycols, cetyl alcohol, cetostearyl alcohol, stearyl alcohol, aryl alkyl polyether alcohols, polyoxyethylene-polyoxypropylene copolymers, poloxamines, cellulose, methylcellulose, hydroxylmethylcellulose, hydroxypropylcellulose, hydroxypropylmethylcellulose, polysaccharides, starch and their derivatives, hydroxyethylstarch, polyvinyl alcohol (PVA), polyvinylpyrrolidone, and their combination thereof); and 2) ionic surfactants (e.g., phospholipids, amphiphilic lipids, 1,2-dialkylglycero-3-alkylphophocholines, 1, 2-distearoyl-sn-glcero-3-phosphocholine (DSPC), 1,2-distearoyl-sn-glycero-3-phosphoethanolamine-N-[carboxy(polyethylene glycol) (DSPE-PEG), dimethylaminoethanecarbamoyl cheolesterol (DC-Chol), N-[1-(2,3-Dioleoyloxy)propyl]-N,N,N-trimethylammonium (DOTAP), alkyl pyridinium halides, quaternary ammonium compounds, lauryldimethylbenzylammonium, acyl carnitine hydrochlorides, dimethyldioctadecylammonium (DDAB), n-octylamines, oleylamines, benzalkonium, cetyltrimethylammonium, chitosan, chitosan salts, poly(ethylenimine) (PEI), poly(N-isopropyl acrylamide (PNIPAM), and poly (allylamine) (PAH), poly (dimethyldiallylammonium chloride) (PDDA), alkyl sulfonates, alkyl phosphates, alkyl phosphonates, potassium laurate, triethanolamine stearate, sodium lauryl sulfate, sodium dodecylsulfate, alkyl polyoxyethylene sulfates, alginic acid, alginic acid salts, hyaluronic acid, hyaluronic acid salts, gelatins, dioctyl sodium sulfosuccinate, sodium carboxymethylcellulose, cellulose sulfate, dextran sulfate and carboxymethylcellulose, chondroitin sulfate, heparin, synthetic poly(acrylic acid) (PAA), poly (methacrylic acid) (PMA), poly(vinyl sulfate) (PVS), poly(styrene sulfonate) (PSS), bile acids and their salts, cholic acid, deoxycholic acid, glycocholic acid, taurocholic acid, glycodeoxycholic acid, derivatives thereof, and combinations thereof).

The polymer or surfactant of the instant invention may be charged or neutral. In a particular embodiment, the polymer or surfactant is neutral or negatively charged (e.g., poloxamers, polysorbates, phospholipids, and their derivatives).

In a particular embodiment, the polymer or surfactant is an amphiphilic block copolymer or lipid derivative. In a particular embodiment, at least one polymer or surfactant of the nanoparticle is an amphiphilic block copolymer, particularly a copolymer comprising at least one block of poly (oxyethylene) and at least one block of poly(oxypropylene). In a particular embodiment, the polymer or surfactant is a triblock amphiphilic block copolymer. In a particular embodiment, the polymer or surfactant is a triblock amphiphilic block copolymer comprising a central hydrophobic block of polypropylene glycol flanked by two hydrophilic blocks of polyethylene glycol. In a particular embodiment, the surfactant is poloxamer 407.

In a particular embodiment, the amphiphilic block copolymer is a copolymer comprising at least one block of poly(oxyethylene) and at least one block of poly(oxypropylene). In a particular embodiment, the amphiphilic block copolymer is a poloxamer. Examples of poloxamers include, without limitation, Pluronic® L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. In a particular embodiment, the poloxamer is poloxamer 407 (Pluronic® F127).

In a particular embodiment of the invention, the polymer or surfactant is present in the nanoparticle and/or solution to synthesize the nanoparticle (as described herein) at a concentration ranging from about 0.0001% to about 10% or 15% by weight. In a particular embodiment, the concentration of the polymer or surfactant ranges from about 0.01% to about 15%, about 0.01% to about 10%, about 0.1% to about 10%, or about 0.1% to about 6% by weight. In a particular embodiment, the nanoparticle comprises at least about 50%, 75%, 80%, 85%, 90%, 95%, 97%, 98%, 99% or higher therapeutic agent (prodrug) by weight. In a particular embodiment, the nanoparticles comprise a defined drug: polymer/surfactant ratio. In a particular embodiment, the drug:polymer/surfactant ratio (e.g., by weight) is from about 10:6 to about 1000:6, about 20:6 to about 500:6, about 50:6 to about 200:6, or about 100:6.

As stated hereinabove, the polymer or surfactant of the instant invention may be linked to a targeting ligand. The targeting of the nanoparticles (e.g., to macrophage) can provide for superior targeting, decreased excretion rates, decreased toxicity, and prolonged half-life compared to free drug or non-targeted nanoparticles. A targeting ligand is a compound that specifically binds to a specific type of tissue or cell type (e.g., in a desired target:cell ratio). For example, a targeting ligand may be used for engagement or binding of a target cell (e.g., a macrophage) surface marker or receptor which may facilitate its uptake into the cell (e.g., within a protected subcellular organelle that is free from metabolic degradation). In a particular embodiment, the targeting ligand is a ligand for a cell surface marker/receptor. The targeting ligand may be an antibody or antigen-binding fragment thereof immunologically specific for a cell surface marker (e.g., protein or carbohydrate) preferentially or exclusively expressed on the targeted tissue or cell type. The targeting ligand may be linked directly to the polymer or surfactant or via a linker. Generally, the linker is a chemical moiety comprising a covalent bond or a chain of atoms that covalently attaches the ligand to the polymer or surfactant. The linker can be linked to any synthetically feasible position of the ligand and the polymer or surfactant. Exemplary linkers may comprise at least one optionally substituted; saturated or unsaturated; linear, branched or cyclic aliphatic group, an alkyl group, or an optionally substituted aryl group. The linker may be a lower alkyl or aliphatic. The linker may also be a polypeptide (e.g., from about 1 to about 10 amino acids, particularly about 1 to about 5). In a particular embodiment, the targeting moiety is linked to either or both ends of the polymer or surfactant. The linker may be non-degradable and may be a covalent bond or any other chemical structure which cannot be substantially cleaved or cleaved at all under physiological environments or conditions.

The nanoparticles/nanoformulations of the instant invention may comprise targeted and/or non-targeted polymers or surfactants. In a particular embodiment, the molar ratio of targeted and non-targeted polymers or surfactants in the nanoparticles/nanoformulations of the instant invention is from about 0.001 to 100%, about 1% to about 99%, about 5% to about 95%, about 10% to about 90%, about 25% to about 75%, about 30% to about 60%, or about 40%. In a particular embodiment, the nanoparticle comprises only targeted polymers or surfactants. In a particular embodiment, the nanoparticles/nanoformulations of the instant invention comprise a folate targeted polymer or surfactant and a non-targeted version of the polymer or surfactant. In a particular embodiment, the nanoparticles/nanoformulations of the instant invention comprise folate-poloxamer 407 (FA-P407) and/or poloxamer 407.

Examples of targeting ligands include but are not limited to macrophage targeting ligands, CD4+ T cell targeting ligands, dendritic cell targeting ligands, and tumor targeting ligands. In a particular embodiment, the targeting ligand is a macrophage targeting ligand. The targeted nanoformulations of the instant invention may comprise a targeting ligand for directing the nanoparticles to HIV tissue and cellular sanctuaries/reservoirs (e.g., central nervous system, gut associated lymphoid tissues (GALT), CD4+ T cells, macrophages, dendritic cells, etc.). Macrophage targeting ligands include, without limitation, folate receptor ligands (e.g., folate (folic acid) and folate receptor antibodies and fragments thereof (see, e.g., Sudimack et al. (2000) Adv. Drug Del. Rev., 41:147-162)), mannose receptor ligands (e.g., mannose), formyl peptide receptor (FPR) ligands (e.g., N-formyl-Met-Leu-Phe (fMLF)), and tuftsin (the tetrapeptide Thr-Lys-Pro-Arg). Other targeting ligands include, without limitation, hyaluronic acid, gp120 and peptide fragments thereof, and ligands or antibodies specific for CD4, CCR5, CXCR4, CD7, CD111, CD204, CD49a, CD29, CD19, CD20, CD22, CD171, CD33, Leis-Y, WT-1, ROR1, MUC16, MUC1, MUC4, estrogen receptor, transferrin receptors, EGF receptors (e.g. HER2), folate receptor, VEGF receptor, FGF receptor, androgen receptor, NGR, Integrins, and GD2. In a particular embodiment, the targeting ligand is folic acid.

As stated hereinabove, the nanoparticles of the instant invention may comprise a further therapeutic agent. The instant invention also encompasses therapeutic methods wherein the prodrug and/or nanoparticles of the instant invention are co-administered with another therapeutic agent. In a particular embodiment, the therapeutic agent is hydrophobic, a water insoluble compound, or a poorly water soluble compound, particularly when included in the nanoparticle. For example, the therapeutic agent may have a solubility of less than about 10 mg/ml, less than 1 mg/ml, more particularly less than about 100 µg/ml, and more particularly less than about 25 µg/ml in water or aqueous media in a pH range of 0-14, preferably between pH 4 and 10, particularly at 20° C.

In a particular embodiment, the therapeutic agent is an antiviral or an antiretroviral. The antiretroviral may be effective against or specific to lentiviruses. Lentiviruses include, without limitation, human immunodeficiency virus (HIV) (e.g., HIV-1, HIV-2), bovine immunodeficiency virus (BIV), feline immunodeficiency virus (Hy), simian immunodeficiency virus (SIV), and equine infectious anemia virus (EIA). In a particular embodiment, the therapeutic agent is an anti-HIV agent. An anti-HIV compound or an anti-HIV agent is a compound which inhibits HIV (e.g., inhibits HIV replication and/or infection). Examples of anti-HIV agents include, without limitation:

(I) Nucleoside-analog reverse transcriptase inhibitors (NRTIs). NRTIs refer to nucleosides and nucleotides and analogues thereof that inhibit the activity of reverse transcriptase, particularly HIV-1 reverse transcriptase. NRTIs comprise a sugar and base. Examples of nucleoside-analog reverse transcriptase inhibitors include, without limitation, adefovir dipivoxil, adefovir, lamivudine, telbivudine, entecavir, tenofovir, stavudine, abacavir, didanosine, emtricitabine, zalcitabine, and zidovudine.

(II) Non-nucleoside reverse transcriptase inhibitors (NNRTIs). NNRTIs are allosteric inhibitors which bind reversibly at a nonsubstrate-binding site on reverse transcriptase, particularly the HIV reverse transcriptase, thereby altering the shape of the active site or blocking polymerase activity. Examples of NNRTIs include, without limitation, delavirdine (DLV, BHAP, U-90152; Rescriptor®), efavirenz (EFV, DMP-266, SUSTIVA®), nevirapine (NVP, Viramune®), PNU-142721, capravirine (S-1153, AG-1549), emivirine (+)-calanolide A (NSC-675451) and B, etravirine (ETR, TMC-125, Intelence®), rilpivirne (RPV, TMC278, Edurant™) DAPY (TMC120), doravirine (Pifeltro™), BILR-355 BS, PHI-236, and PHI-443 (TMC-278).

(III) Protease inhibitors (PI). Protease inhibitors are inhibitors of a viral protease, particularly the HIV-1 protease. Examples of protease inhibitors include, without limitation, darunavir, amprenavir (141W94, AGEN-ERASE®), tipranivir (PNU-140690, APTIVUS®), indinavir (MK-639; CRIXIVAN®), saquinavir (INVIRASE®, FORTOVASE®), fosamprenavir (LEXIVA®), lopinavir (ABT-378), ritonavir (ABT-538, NORVIR®), atazanavir (REYATAZ®), nelfinavir (AG-1343, VIRACEPT®), lasinavir (BMS-234475/CGP-61755), BMS-2322623, GW-640385X (VX-385), AG-001859, and SM-309515.

(IV) Fusion or entry inhibitors. Fusion or entry inhibitors are compounds, such as peptides, which block HIV entry into a cell (e.g., by binding to HIV envelope protein and blocking the structural changes necessary for the virus to fuse with the host cell). Examples of fusion inhibitors include, without limitation, CCR5 receptor antagonists (e.g., maraviroc (Selzentry®, Celsentri)), enfuvirtide (INN, FUZEON®), T-20 (DP-178, FUZEON®) and T-1249.

(V) Integrase inhibitors (in addition to the prodrug of the instant invention). Integrase inhibitors are a class of antiretroviral drug designed to block the action of integrase (e.g., HIV integrase), a viral enzyme that inserts the viral genome into the DNA of the host cell. Examples of integrase inhibitors include, without limitation, raltegravir, elvitegravir, GSK1265744 (cabotegravir), GSK1349572 (dolutegravir), GS-9883 (bictegravir), and MK-2048.

Anti-HIV compounds also include maturation inhibitors (e.g., bevirimat). Maturation inhibitors are typically compounds which bind HIV gag and disrupt its processing during the maturation of the virus. Anti-HIV compounds also include HIV vaccines such as, without limitation, ALVAC® HIV (vCP1521), AIDSVAX®B/E (gp120), and combinations thereof. Anti-HIV compounds also include HIV antibodies (e.g., antibodies against gp120 or gp41), particularly broadly neutralizing antibodies.

More than one anti-HIV agent may be used, particularly where the agents have different mechanisms of action (as outlined above). For example, anti-HIV agents which are not NNRTIs may be combined with the NNRTI prodrugs of the instant invention. In a particular embodiment, the anti-HIV therapy is highly active antiretroviral therapy (HAART).

The instant invention encompasses compositions (e.g., pharmaceutical compositions) comprising at least one prodrug and/or nanoparticle of the instant invention and at least one pharmaceutically acceptable carrier. As stated hereinabove, the nanoparticle may comprise more than one therapeutic agent. In a particular embodiment, the pharmaceutical composition comprises a first nanoparticle comprising a first prodrug and a second nanoparticle comprising a second prodrug, wherein the first and second prodrugs are different. In a particular embodiment, the first prodrug is a prodrug of the instant invention and the second prodrug is a prodrug of a non-nucleoside reverse transcriptase inhibitor (NNRTI), particularly rilpivirine (RPV). The compositions (e.g., pharmaceutical compositions) of the instant invention may further comprise other therapeutic agents (e.g., other anti-HIV compounds (e.g., those described herein)).

The present invention also encompasses methods for preventing, inhibiting, and/or treating a disease or disorder. The methods comprise administering a prodrug and/or nanoparticle of the instant invention (optionally in a composition) to a subject in need thereof. In a particular embodiment, the disease or disorder is a viral (e.g., retroviral) infection. Examples of viral infections include, without limitation: HIV, Hepatitis B, Hepatitis C, and HTLV. In a particular embodiment, the viral infection is a retroviral or lentiviral infection, particularly an HIV infection (e.g., HIV-1).

The prodrugs and/or nanoparticles of the instant invention (optionally in a composition) can be administered to an animal, in particular a mammal, more particularly a human, in order to treat/inhibit/prevent the disease or disorder (e.g., a retroviral infection such as an HIV infection). The pharmaceutical compositions of the instant invention may also comprise at least one other therapeutic agent such as an antiviral agent, particularly at least one other anti-HIV compound/agent. The additional anti-HIV compound may also be administered in a separate pharmaceutical composition from the prodrugs or compositions of the instant invention. The pharmaceutical compositions may be administered at the same time or at different times (e.g., sequentially).

The dosage ranges for the administration of the prodrugs, nanoparticles, and/or compositions of the invention are those large enough to produce the desired effect (e.g., curing, relieving, treating, and/or preventing the disease or disorder (e.g., HIV infection), the symptoms of it (e.g., AIDS, ARC), or the predisposition towards it). In a particular embodiment, the pharmaceutical composition of the instant invention is administered to the subject at an amount from about 5 µg/kg to about 500 mg/kg. In a particular embodiment, the pharmaceutical composition of the instant invention is administered to the subject at an amount greater than about 5 µg/kg, greater than about 50 µg/kg, greater than about 0.1 mg/kg, greater than about 0.5 mg/kg, greater than about 1 mg/kg, or greater than about 5 mg/kg. In a particular embodiment, the pharmaceutical composition of the instant invention is administered to the subject at an amount from about 0.5 mg/kg to about 100 mg/kg, about 10 mg/kg to about 100 mg/kg, or about 15 mg/kg to about 50 mg/kg. The dosage should not be so large as to cause significant adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

The prodrugs and nanoparticles described herein will generally be administered to a patient as a pharmaceutical composition. The term "patient" as used herein refers to human or animal subjects. These prodrugs and nanoparticles may be employed therapeutically, under the guidance of a physician.

The pharmaceutical compositions comprising the prodrugs and/or nanoparticles of the instant invention may be conveniently formulated for administration with any pharmaceutically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents, or suitable mixtures thereof, particularly an aqueous solution. The concentration of the prodrugs and/or nanoparticles in the chosen medium may be varied and the medium may be chosen based on the desired route of administration of the pharmaceutical composition. Except insofar as any conventional media or agent is incompatible with the nanoparticles to be administered, its use in the pharmaceutical composition is contemplated.

The dose and dosage regimen of prodrugs and/or nanoparticles according to the invention that are suitable for administration to a particular patient may be determined by a physician considering the patient's age, sex, weight, general medical condition, and the specific condition for which the nanoparticles are being administered and the severity thereof. The physician may also take into account the route of administration, the pharmaceutical carrier, and the nanoparticle's biological activity.

Selection of a suitable pharmaceutical composition will also depend upon the mode of administration chosen. For example, the nanoparticles of the invention may be administered by direct injection or intravenously. In this instance, a pharmaceutical composition comprises the prodrug and/or nanoparticle dispersed in a medium that is compatible with the site of injection.

Prodrugs and/or nanoparticles of the instant invention may be administered by any method. For example, the prodrugs and/or nanoparticles of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the prodrug and/or nanoparticle is parenterally. In a particular embodiment, the prodrug and/or nanoparticle is administered orally, intramuscularly, subcutaneously, or to the bloodstream (e.g., intravenously). In a particular embodiment, the prodrug and/or nanoparticle is administered intramuscularly or subcutaneously. Pharmaceutical compositions for injection are known in the art. If injection is selected as a method for administering the prodrug and/or nanoparticle, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing a prodrug and/or nanoparticle of the present invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, oral, direct injection, intracranial, and intravitreal.

A pharmaceutical composition of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. In a particular embodiment, the prodrugs and/or nanoparticles of the instant invention, due to their long-acting therapeutic effect, may be administered once every 1 to 12 months or even less frequently. For example, the nanoformulations of the instant invention may be administered once every 0.5, 1, 2, 3, 4, 5, 6, 7, 8, 9, 10, 11, 12, 15, 18, 21, 24, or more months. In a particular embodiment, the prodrugs and/or nanoparticles of the instant invention are administered less than once every two months. In a particular embodiment, the prodrugs and/or nanoformulations of the prodrugs are administered once every month, once every two months, particularly once every three months, once every four months, once every five months, once every six months, once every seven months, once every eight months, once every nine months, once every ten months, once every eleven months, once every twelve months, or less frequently.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of nanoparticles may be determined by evaluating the toxicity of the molecules or cells in animal models. Various concentrations of nanoparticles in pharmaceutical composition may be administered to mice, and the minimal and maximal dosages may be determined based on the beneficial results and side effects observed as a result of the treatment. Appropriate dosage unit may also be determined by assessing the efficacy of the nanoparticle treatment in combination with other standard drugs. The dosage units of nanoparticle may be determined individually or in combination with each treatment according to the effect detected.

The pharmaceutical composition comprising the nanoparticles may be administered at appropriate intervals until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a pharmaceutical composition comprising a prodrug and/or nanoparticle of the instant invention and, preferably, at least one pharmaceutically acceptable carrier. The instant invention also encompasses methods wherein the subject is treated via ex vivo therapy. In particular, the method comprises removing cells from the subject, exposing/contacting the cells in vitro to the nanoparticles of the instant invention, and returning the cells to the subject. In a particular embodiment, the cells comprise macrophage. Other methods of treating the disease or disorder may be combined with the methods of the instant invention may be co-administered with the pharmaceutical compositions of the instant invention.

The instant also encompasses delivering the nanoparticle of the instant invention to a cell in vitro (e.g., in culture). The nanoparticle may be delivered to the cell in at least one carrier.

Definitions

The following definitions are provided to facilitate an understanding of the present invention.

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "prodrug" refers to a compound that is metabolized or otherwise converted to a biologically active or more active compound or drug, typically after administration. A prodrug, relative to the drug, is modified chemically in a manner that renders it, relative to the drug, less active, essentially inactive, or inactive. However, the chemical modification is such that the corresponding drug is generated by metabolic or other biological processes, typically after the prodrug is administered.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a retroviral infection results in at least an inhibition/reduction in the number of infected cells and/or detectable viral levels.

As used herein, the term "prevent" refers to the prophylactic treatment of a subject who is at risk of developing a condition (e.g., HIV infection) resulting in a decrease in the probability that the subject will develop the condition.

A "therapeutically effective amount" of a compound or a pharmaceutical composition refers to an amount effective to prevent, inhibit, treat, or lessen the symptoms of a particular disorder or disease. The treatment of a microbial infection (e.g., HIV infection) herein may refer to curing, relieving, and/or preventing the microbial infection, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "highly active antiretroviral therapy" (HAART) refers to HIV therapy with various combinations of therapeutics such as nucleoside reverse transcriptase inhibitors, non-nucleoside reverse transcriptase inhibitors, HIV protease inhibitors, and fusion inhibitors.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). "Hydrophobic" compounds are, for the most part, insoluble in water. As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

An "antibody" or "antibody molecule" is any immunoglobulin, including antibodies and fragments thereof (e.g., scFv), that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "targeting ligand" refers to any compound which specifically binds to a specific type of tissue or cell type, particularly without substantially binding other types of tissues or cell types. Examples of targeting ligands include, without limitation: proteins, polypeptides, peptides, antibodies, antibody fragments, hormones, ligands, carbohydrates, steroids, nucleic acid molecules, and polynucleotides.

The term "aliphatic" refers to a non-aromatic hydrocarbon-based moiety. Aliphatic compounds can be acyclic (e.g., linear or branched) or cyclic moieties (e.g., cycloalkyl) and can be saturated or unsaturated (e.g., alkyl, alkenyl, and alkynyl). Aliphatic compounds may comprise a mostly carbon main chain (e.g., 1 to about 30 carbons) and comprise heteroatoms and/or substituents (see below). The term "alkyl," as employed herein, includes saturated or unsaturated, straight or branched chain hydrocarbons containing 1 to about 30 carbons in the normal/main chain. The hydrocarbon chain of the alkyl groups may be interrupted with one or more heteroatom (e.g., oxygen, nitrogen, or sulfur). An alkyl (or aliphatic) may, optionally, be substituted (e.g. with fewer than about 8, fewer than about 6, or 1 to about 4 substituents). The term "lower alkyl" or "lower aliphatic" refers to an alkyl or aliphatic, respectively, which contains 1 to 3 carbons in the hydrocarbon chain. Alkyl or aliphatic substituents include, without limitation, alkyl (e.g., lower alkyl), alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)$— or $NHRC(=O)$—, wherein R is an alkyl), urea (—$NHCONH_2$), alkylurea, aryl, ether, ester, thioester, nitrile, nitro, amide, carbonyl, carboxylate and thiol. Aliphatic and alkyl groups having at least about 5 carbons in the main chain are generally hydrophobic, absent extensive substitutions with hydrophilic substituents.

The term "aryl," as employed herein, refers to monocyclic and bicyclic aromatic groups containing 6 to 10 carbons in the ring portion. Examples of aryl groups include, without limitation, phenyl or naphthyl, such as 1-naphthyl and 2-naphthyl, or indenyl. Aryl groups may optionally include one to three additional rings fused to a cycloalkyl ring or a heterocyclic ring. Aryl groups may be optionally substituted through available carbon atoms with, for example, 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, or substituted amino. The aryl group may be a heteroaryl. "Heteroaryl" refers to an optionally substituted, mono-, di-, tri-, or other multicyclic aromatic ring system that includes at least one, and preferably from 1 to about 4, sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred.

The following examples provide illustrative methods of practicing the instant invention and are not intended to limit the scope of the invention in any way.

Example 1

Maximal reduction of residual HIV-1 from its tissue sanctuary sites that include brain, lymph nodes, bone marrow, gut-associated lymphoid tissue and the genital tracts can be achieved by development of long acting reservoir targeted medicines. In addition to the benefit of infrequent dosing intervals, long acting injectable drug formulations can be designed to utilize receptor mediated processes to achieve improved cell targeting, extended drug half-life, and enhanced tissue biodistribution. CAB is a potent viral integrase inhibitor and has been formulated as a LAP (CAB-LAP) which demonstrates sustained plasma drug levels in humans after single intramuscular dose. Long-acting injectable nanoformulations of rilpivirine and CAB-LAP have already enabled once-monthly injection for HIV suppression and prevention (Andrews, et al. (2014) Science 343(6175): 1151-1154; Cohen, J. (2014) Science 343(6175):1067; Spreen, et al. (2013) Curr. Opin. HIV AIDS, 8(6):565-571). The main limitations of existing nanoformulations include requirement for high doses and high injection volumes. To this end, long acting slow effective release antiretroviral therapies (LASER ART) have been developed by synthesizing lipophilic and hydrophobic prodrug nanocrystals that permit rapid drug penetration across physiological barriers. LASER ART maximizes drug loading with limited excipient usage, while maintaining scalability and long-term storage. Myristoylated prodrugs have been formulated with poloxamer surfactants. Improved potency, bioavailability, and tissue distribution of CAB was demonstrated by increasing drug lipophilicity that sustained plasma CAB concentrations at the PA-IC$_{90}$ for 4 months in rhesus macaques after single 45 mg/kg CAB equivalent intramuscular injection. Here, improved prodrugs and nanoformulations have been synthesized which reduce dosing frequency while improving viral reservoir targeting and drug activity.

A potent ester prodrug of CAB is provided herein which has physicochemical properties which allows the use of a LASER ART formulation for infrequent administration, such as once every six to twelve months dosing intervals or even less frequently. The criteria evaluated in selecting an optimal CAB prodrug candidate included drug potency, lipophilicity profile, efficient in vivo conversion to CAB with minimal systemic prodrug circulation, and sustained CAB concentrations four times above the PA-IC$_{90}$ for periods of six months or longer after a single intramuscular injection of the prodrug formulation. Surprisingly, the instant invention has demonstrated that variation in the hydrocarbon chain length of the fatty ester prodrug dramatically improves active drug release and retention. This culminated in the identification of M2CAB, an 18-carbon fatty ester prodrug of CAB, with unexpectedly superior controlled release kinetics of CAB when compared to MCAB or other fatty acid hydrocarbon chain lengths.

The prodrugs of the instant invention are derivatives of an integrase inhibitor such as CAB conjugated to hydrophobic cleavable moieties. Thus, the hydrophobic parent compound is converted into a more hydrophobic ester derivative. This is achieved through attachment of a fatty acid moiety that can improve drug protein binding and bioavailability. The ester linkage between the integrase inhibitor (e.g., CAB) and derivatizing moieties is prone to enzymatic or hydrolytic cleavage. The mechanism of drug release from the particle involves dissolution of the prodrug from the excipient followed by efficient ester degradation to generate the active parent compound. The developed NM2CAB significantly improved drug uptake by MDM with sustained drug retention over a 30-day observation period; whereas NCAB or NMCAB formulations were eliminated from macrophages after a single day or 20 days of treatment, respectively. Similarly, MDM treated with NM2CAB exhibited enhanced and sustained antiretroviral activities compared to NCAB or NMCAB when challenged with HIV-1 for up to 30 days after single drug treatment. HIV-1p24 was not detected in the NM2CAB treated group at any of these time points. The benefits of the system include unexpectedly improved drug bioavailability and extended half-life. NM2CAB prolonged plasma and tissue CAB concentrations demonstrate that an effective once every six-months dosing interval can be achieved.

Synthesis of M2CAB

Synthesis of M2CAB prodrugs was performed as depicted:

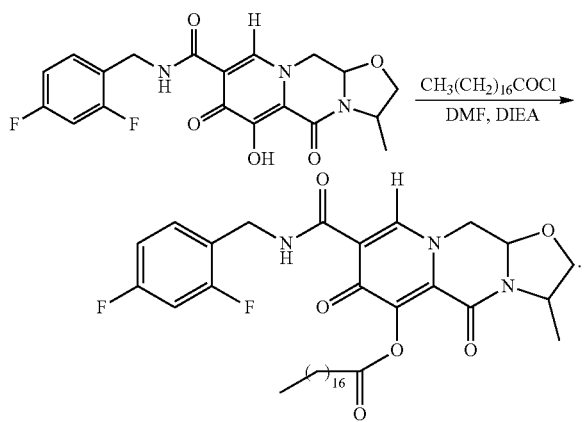

Briefly, the preparation of the M2CAB prodrug was performed by: 1) deprotonation of the phenol functional group with a suitable base such as N,N-diisopropylethylamine; and 2) reaction with either acyl chloride or activated carboxylic acid of the alkyl fatty acid.

Both steps 1 and 2 were performed in a single vessel. Specifically, the hydroxyl group was deprotonated using the appropriate reagent. The alcohol anion was then coupled with the fatty acyl chloride or activated carboxylic acid to generate the prodrugs. Examples of coupling reagents that can be used to activate the carboxylic acid include, without limitation, uranium salts, carbodiimide reagents, and phosphonium salts. An example of the base that can be used in the coupling reaction is, without limitation, N,N diisopropylethylamine (DIEA). Examples of polar aprotic solvents that can be used include, without limitation, N,N-dimethylformamide (DMF), tetrahydrofuran (THF), and acetonitrile. The reagents were mixed at 0° C. and gradually warmed to temperature over 12-24 hours. The final compounds were purified on a silica column chromatography and characterized by nuclear magnetic resonance spectroscopy and high performance liquid chromatography in tandem with mass spectrometry.

Hydroxyl Group Deprotonation and Coupling to Fatty Acid

A solution of CAB (2 g, 4.93 mmol, 1.0 equiv.) in anhydrous dimethylformamide (20 mL) was cooled to 0° C. under argon. N,N diisopropylethylamine (1.7 mL, 9.86 mmol, 2.0 equiv.) was then added dropwise to the precooled solution of the drug. Stearoyl chloride (3.3 mL, 9.86 mmol, 2.0 equiv.) was then added to the deprotonated phenol solution. The mixture was gradually warmed to room temperature under stirring over 16 hours, concentrated, and purified by flash chromatography eluting with 80 to 90% EtOAc/Hex to give the prodrug in a chemical yield of 90%. The $^1$H-NMR spectrum of M2CAB showing the presence of a broad peak at 1.20-1.50 ppm and those corresponding to the aliphatic protons on the fatty acid moiety.

Formulation Synthesis

M2CAB nanocrystals were coated with poloxamer 407 (P407), 1,2-distearoyl-sn-glycero-3-phosphocholine (DSPC), 1,2-distearoyl-sn-glycero-3-phosphoethanolamine-N-[carboxy(polyethylene glycol)-2000 (DSPE-PEG), and/ or polyvinyl alcohol (PVA). The nanocrystals may also be stabilized with polysorbate and polyethylene glycol surfactants. Based on proton NMR spectroscopy data, a drug to surfactant ratio of 100:6 by weight was used to manufacture nanoformulated M2CAB, MCAB and CAB. Briefly, 1-5% (w/v) M2CAB, MCAB or CAB and 0.06-0.3% (w/v) P407 were mixed in endotoxin free water. The premixed suspensions were formulated by wet milling or high-pressure homogenization at 20,000 psi pressure until desirable size and polydispersity index (PDI) were achieved. Nanoformulations were characterized for particle size, polydispersity index (PDI) and zeta potential by dynamic light scattering (FIG. 1). This was done using a Malvern Zetasizer, Nano Series Nano-ZS (Malvern Instruments Inc, Westborough, Mass.). Nanoparticle morphology was determined by scanning electron microscopy (SEM). UPLC MS/MS was used for drug quantitation.

Macrophage Uptake and Retention

Human monocytes were obtained by leukapheresis from HIV-1/2 and hepatitis B seronegative donors and then purified by counter-current centrifugal elutriation (Balkundi et al., Intl. J. Nanomed. (2011) 6:3393-3404; Nowacek et al., Nanomed. (2009) 4(8):903-917). Human monocytes were plated in a 12-well plate at a density of $1.0 \times 10^6$ cells per well using DMEM supplemented with 10% heat-inactivated pooled human serum, 1% glutamine, 10 µg/mL ciprofloxacin, and 50 µg/mL gentamicin. Cells were maintained at 37° C. in a 5% $CO_2$ incubator. After 7-10 days of differentiation in the presence of 1000 U/mL recombinant human macrophage colony stimulating factor (MCSF), MDM were treated with a range of nanoformulations and native drugs. Uptake of drug was assessed by measurements of intracellular drug concentrations at various timepoints after treatment. For drug retention studies, cells were treated for 8 hours then washed with PBS and maintained with half-media changes every other day until collection at the indicated timepoints. For both studies, adherent MDM were washed with PBS (3×1 mL), then scraped into 1 mL of fresh PBS, and counted at indicated time points using a Countess™ automated cell counter (Invitrogen, Carlsbad, Calif.). Cells were pelleted by centrifugation at 950×g for 8 minutes at 4° C. The cell pellet was reconstituted in 200 µl of high performance liquid chromatography (HPLC)-grade methanol and probe sonicated followed by centrifugation at 20,000×g for 20 minutes. The supernatant was analyzed for drug content using HPLC.

As seen in FIG. 2A, NM2CAB was taken up by MDM to statistically higher levels than NMCAB. Moreover, MDM retained NM2CAB at statistically higher levels for longer periods of time than NMCAB (FIG. 2A).

Antiretroviral Activities

Antiretroviral efficacy was determined by measurements of HIV reverse transcriptase (RT) activity (FIGS. 2B and 2C). To assess antiretroviral efficacy, MDM were treated with either 100 µM CAB-LAP, NMCAB or NM2CAB for 8 hours. After treatment, cells were washed with PBS to remove excess of free drug and nanoparticles and the cells were cultured with fresh media, with half-media exchanges every other day. The MDM were challenged with HIV-1$_{ADA}$ at a MOI of 0.01 infectious viral particles/cell for up to 30 days. Progeny virion production was measured by RT activity in culture medium (Kalter, et al. (1992) J. Clin. Microbiol., 30(4):993-995). HIV-1 p24 protein antigen expression was assessed (Guo, et al. (2014) J. Virol., 88(17):9504-9513). The MDM were washed with PBS and fixed with 4% paraformaldehyde for 15 minutes at room temperature. The cells were blocked using 10% BSA containing 1% Triton X-100 in PBS for 30 minutes at room temperature. Following blocking, cells were incubated with HIV-1 p24 mouse monoclonal antibodies (1:50; Dako, Carpinteria, Calif., USA) for overnight at 4° C., followed by 1 hour incubation at room temperature. HRP-labeled polymer anti-mouse secondary antibody (Dako EnVision® System) was added (one drop/well). Hematoxylin was added to counterstain the nuclei and images were captured using a Nikon TE300 microscope with a 20× objective. As seen in FIGS. 2B and 2C, unexpectedly superior antiretroviral efficacy was observed for nanoformulated M2CAB compared to nanoformulated CAB or MCAB.

Pharmacokinetic/Biodistribution Study

Female NSG mice were administered a single IM 45 mg/kg CAB equivalent dose of NM2CAB, NMCAB or NCAB. Drug levels from plasma and tissues were assayed by UPLC-MS/MS. Drug levels in plasma were monitored weekly. A single IM injection of NM2CAB demonstrates zero order controlled release kinetics of active CAB that remain four times above the PA-IC$_{90}$ when compared to NMCAB or NCAB (FIG. 3). At day 364 after injection, plasma CAB levels were at 345.2 ng/ml for NM2CAB, 8.5 ng/ml for NMCAB, and undetectable values for NCAB (limit of detection of 0.5 ng/ml).

Mice were also administered a single IM 45 mg/kg CAB equivalent dose of NM3CAB (C22). Drug levels in plasma were monitored weekly. At day 28 after injection, plasma CAB levels were at 233.2 ng/ml (FIG. 3B). Accordingly, it is clear that NM2CAB (C18) was statistically superior to the shorter NMCAB (C14) and the longer NM3CAB (C22) for maintaining long term, effective release of drug.

The hydrophobicity of CAB was greatly improved upon derivatization into M2CAB prodrug. The improved hydrophobicity of M2CAB facilitated production of stable formulations with high drug loading capacity. Moreover, the conversion of CAB into the more hydrophobic M2CAB and nanoparticle formation significantly improved intracellular accumulation of the drug compared to nanoformulated CAB or MCAB. Significant improvements in MDM retention and antiretroviral efficacy were also observed for nanoformulated M2CAB compared to nanoformulated CAB or MCAB. A single IM injection of NM2CAB at 45 mg CAB equivalents/kg in female NSG mice also unexpectedly demonstrated plasma CAB concentrations four times above the PA-IC$_{90}$ for more than five months, which is significantly greater than nanoformulated CAB or MCAB.

Example 2

Current antiretroviral drug (ARV) therapeutic regimens are both potent and well-tolerated enabling sustained, life-long suppression of human immunodeficiency virus type one (HIV-1) (Fauci, et al., JAMA (2019) 321:844-845). However, such control of viral replication must be linked to regimen adherence, which in turn, is affected by concurrent co-morbidity, social stigma, behavior, concurrent illicit drug-use and cost (Fauci, et al., JAMA (2019) 321:844-845). Nevertheless, even strict adherence to daily dosing commonly lead to drug toxicities, drug-drug interactions and the emergence of viral-drug resistance. All drug regimens preclude viral elimination (Dash, et al., Nat. Commun. (2019) 10:2753). This highlights the fact that all therapies require life-long adherence to sustain HIV-1 suppression and mitigate disease. These have led scientists to develop long acting (LA) therapeutic approaches. All focus on improving regimen adherence and drug potency (Gendelman, et al., Trends Microbiol. (2019) 27:593-606). The two most active and those nearing Food and Drug Administration USA clinical approvals are ARV LA injectables while implantable drug devices remain in development (Margolis, et al., Lancet (2017) 390:1499-1510; Taylor, et al., Topics Antiviral Med. (2019) 27:50-68).

Studies performed, to date, have held considerable promise for LA injectable for wide spread human use (Margolis, et al., Lancet (2017) 390:1499-1510; Taylor, et al., Topics Antiviral Med. (2019) 27:50-68; Kerrigan, et al., PloS One (2018) 13:e0190487). As a result, LA injectable nanoformulations of cabotegravir (CAB) and rilpivirine (RPV) as a two-drug combination will see approval for monthly administration likely by the end of 2019 (Margolis, et al., Lancet (2017) 390:1499-1510; Taylor, et al., Topics Antiviral Med. (2019) 27:50-68; Kerrigan, et al., PloS One (2018) 13:e0190487). The "Antiretroviral Therapy as Long-Acting Suppression" (ATLAS) and "First Long-Acting Injectable Regimen" (FLAIR) both demonstrated promising safety, efficacy and tolerability (Taylor, et al., Topics Antiviral Med. (2019) 27:50-68). Combination treatment affirmed non-inferiority when treatment was compared against standard oral three-drug regimens (Taylor, et al., Topics Antiviral Med. (2019) 27:50-68). Likewise, drug implants have also shown promise (Kovarova, et al., Nat. Commun. (2018) 9:4156; Gunawardana, et al., Antimicrob. Agents Chemother. (2015) 59:3913-3919; Flexner, C., Curr. Opin. HIV AIDS (2018) 13:374-380; Barrett, et al., Antimicrob. Agents Chemother. (2018) 62(10):e01058-18.). However, limitations abound for both approaches including injection site reactions, large injection volumes, dosage frequency, limited penetrance into viral reservoirs (Margolis, et al., Lancet (2017) 390:1499-1510; Markowitz, et al., Lancet HIV (2017) 4:e331-e340; Zhou, et al., Biomaterials (2018) 151:53-65). Moreover, these newer therapeutic approaches require frequent professional health care services either by providing the injections themselves or performing implant insertions and removals. Measurements of tissue and plasma drug-levels correlates LA ARV efficacy that include drug penetrance into mucosal, lymphoid tissues and the central nervous system as well as long-term safety. Based on the extent of these unknowns, there is an immediate need for further improvements in LA ARV regimens. Any future LA ARVs need to be administered in reduced volumes without systemic toxicity. If achieved, ARV regimens could also behave in manners reflective of an ARV vaccine mimetic. Success would prevent new infections and reduce new transmission, and in such manners could achieve a functional HIV-1 cure.

To such ends, LA ARV libraries have been created for a spectrum of antiretroviral agents (Zhou, et al., Biomaterials (2018) 151:53-65; Hilaire, et al., J. Control Release (2019) 311-312:201-211; Ibrahim, et al., Int. J. Nanomedicine (2019) 14:6231-6247; Lin, et al., Chem. Commun. (Camb) (2018) 54:8371-8374; McMillan, et al., Antimicrob. Agents Chemother. (2017) 62: e01316-17; McMillan, et al., AIDS (2019) 33:585-588; Sillman, et al., Nat. Commun. (2018) 9:443; Smith, et al., Biomaterials (2019) 223:119476; Soni, et al., Biomaterials (2019) 222:119441). Herein, CAB prodrugs were created with the aim of prolonging the drug's apparent half-life and antiretroviral activities while exerting tight control of hydrolysis. The synthesis and comprehensive physiochemical characterization of three prodrugs of CAB with 14, 18 and 22 carbon linker arms (MCAB, M2CAB, and M3CAB, respectively) with complete assessment of their respective nanoformulations (NMCAB, NM2CAB, and NM3CAB) are reported. These analyses extended prior testing of the first generation CAB prodrug, MCAB (Zhou, et al., Biomaterials (2018) 151:53-65;

McMillan, et al., AIDS (2019) 33:585-588). The C18 nanoformulation, NM2CAB, enhanced uptake and retention of CAB in monocyte-macrophages and showed long-term monthly protection against HIV-1 infectious challenge. NM2CAB generated CAB plasma concentrations above 90% of the protein associated inhibitor concentration (PA-IC$_{90}$) of 166 ng/mL for 52 weeks. This correlated with significant lymphoid, mucosal and gut biodistribution levels after a single parenteral injection. There were no recorded systemic adverse events. Parallel drug plasma concentrations in drug injected normal and immunodeficient mice and rhesus monkeys affirmed the long-sustained drug release for prevention and treatment regimens. The results taken together indicate that the prodrugs can be used for the same purpose of a preventative vaccine against HIV-1.

Materials and Methods

Reagents

CAB was purchased from BOC sciences (Shirley, N.Y.). Pyridine, dimethylformamide (DMF), N,N-diisopropylethylamine (DIEA), myristoyl chloride, stearoyl chloride, behenic acid, poloxamer 407 (P407), ciprofloxacin, dimethylthiazol-2-yl)-2,5-diphenyltetrazolium bromide (MTT), dimethyl sulfoxide (DMSO), paraformaldehyde (PFA), and 3,3'-diaminobenzidine (DAB) were purchased from Sigma-Aldrich (St. Louis, Mo.). Diethyl ether, ethyl acetate, hexanes, acetonitrile (ACN), methanol, LC-MS-grade water, cell culture grade water (endotoxin-free), gentamicin, potassium phosphate monobasic (KH$_2$PO$_4$), bovine serum albumin (BSA), Triton™ X-100, and TRIzol® reagent were purchased from Fisher Scientific (Hampton, N.H.). Monoclonal mouse anti-human HIV-1 p24 (clone Kal-1), and the polymer-based HRP-conjugated anti-mouse EnVision™+ secondary were purchased from Dako (Carpinteria, Calif.). Heat-inactivated pooled human serum was purchased from Innovative Biologics (Herndon, Va.). Dulbecco's Modification of Eagle's Medium (DMEM) was purchased from Corning Life Sciences (Tewksbury, Mass.).

Synthesis and Characterization of CAB Prodrugs

A series of three prodrugs was synthesized by esterification of the 10-hydroxyl group on CAB yielding lipophilic prodrugs with 14, 18 and 22 carbon linkers named MCAB, M2CAB, and M3CAB. Initially, CAB was dried from anhydrous pyridine and then suspended in anhydrous DMF. The mixture was cooled to 0° C. under argon. DIEA (2 equivalents) was used to deprotonate the 10-hydroxyl group of CAB, which was further reacted with 2 equivalents myristoyl chloride or stearoyl chloride for 24 hours to obtain MCAB or M2CAB respectively. M3CAB synthesis was a two-step process. In the first step, behenyl chloride was synthesized by chlorination of the carboxylic acid group of behenic acid in anhydrous chloroform using 4 equivalents thionyl chloride. CAB dried from anhydrous pyridine and resuspended in anhydrous DMF in the presence of 4 equivalents trietheylamine was further added to the behenyl chloride in DMF at 0° C. under argon followed by heating the reaction at 50° C. for 24 hours. All the resultant prodrugs were purified by silica gel column chromatography using an initial mobile phase of 4:1 ethyl acetate: hexanes for initial fractions, then 9:1 ethyl acetate:hexanes for the remainder. Finally, the prodrugs were precipitated and washed in diethyl ether, dried under vacuum to obtain a white powder with average yield of 85-95%. Successful synthesis of prodrugs was confirmed by proton and carbon nuclear magnetic resonance ($^1$H and $^{13}$C NMR) spectra recorded by Bruker Avance-III HD (Billerica, Mass.) operating at 500 MHz, a magnetic field strength of 11.7 T. Fourier Transform Infrared analysis (FT-IR) was performed on a universal attenuated total reflectance (UATR) Spectrum Two (PerkinElmer, Waltham, Mass.). Comparative crystallographic analyses of CAB and prodrugs by powder X-ray diffraction (XRD) were carried out in the 2θ range of 2–70° at a rate of 1°/s using PANalytical Empyrean diffractometer (PANalytical Inc., Westborough, Mass.) with Cu-Kα radiation (1.5418 Å) at 40 kV, 45 mA setting. Molecular mass was determined by direct infusion into a Waters TQD mass spectrometer.

UPLC-UV/Vis quantification of CAB, MCAB, M2CAB, and M3CAB

Waters ACQUITY ultra-performance liquid chromatography (UPLC) H-Class system with TUV detector and Empower 3 software (Milford, Mass.) was used to measure drug concentrations. CAB, MCAB, M2CAB, and M3CAB samples were separated on a Phenomenex Kinetex 5 µm C18 column (150×4.6 mm) (Torrance, Calif.). CAB was detected at 254 nm, using a mobile phase consisting of 65% 50 mM potassium phosphate monobasic (KH$_2$PO$_4$), pH 3.2, and 35% acetonitrile (ACN) and a flow rate of 1.0 mL/minute. MCAB, M2CAB, and M3CAB were detected at 230 nm, using a mobile phase consisting of 90% ACN and 10% water, 95% ACN and 5% water, 98% ACN and 2% water, respectively, and a flow rate of 1.0 mL/minute. Drug content was determined relative to peak areas from drug standards (0.05-50 µg/mL) in methanol.

Measures of Drug Formulation Aqueous Solubility

The aqueous solubility of CAB, MCAB, M2CAB and M3CAB in optima water was determined by adding the excess drug or prodrug powder in 1 mL water to make the saturated aqueous solution. The mixture was stirred for 24 hours at room temperature. Further, the solution was centrifuged at 14000 rpm for 10 minutes to pellet the undissolved powder. The supernatant was collected, lyophilized and dissolved in methanol for the drug content analysis by UPLC UV/Vis.

Chemical Stability

The stability of MCAB, M2CAB and M3CAB in acidic (pH 1), basic (pH 11) and neutral (pH 7) conditions at room temperature and elevated temperature (37° C.) was determined. The stock solution of each prodrug was prepared in DMSO at a concentration of 1 mg/mL. For acidic, basic and neutral assays, 100 µL of stock solution of each prodrug was added to 1900 µL of 0.1 M HCl, 0.1 M NaOH or optima-grade water (pH adjusted to 7), respectively. Samples were then incubated at room temperature and 40° C. under shaking conditions (Innova® 42 shaker incubator, 150 rpm). Samples were withdrawn at 0, 2, 4, 8 and 24 hours and stored at −80° C. Later, samples were analyzed for drug content by UPLC-UV/Vis.

Plasma Cleavage Drug Hydrolysis Kinetics

The hydrolysis kinetics of MCAB, M2CAB and M3CAB and relative release of active drug were determined in plasma of different species (mouse, rat, rabbit, monkey, dog, and human). MCAB, M2CAB or M3CAB (1 µM) were incubated in 100 µL plasma at 37° C. At different time points, 1 mL acidified methanol (0.1% formic acid and 25 mM ammonium formate to avoid further prodrug hydrolysis) was added to each sample and vortexed for 3 minutes to stop the reaction. For 0-minute time-point, a 100 µL ice cold plasma was spiked with prodrug stock solution, and 1 ml of ice cold acidic methanol was added immediately. Following the addition of methanol, samples were centrifuged at 15,000 g for 10 minutes, and collected supernatant was analyzed for drug content by UPLC-MS/MS (Waters Xevo TQ-XS).

Nanoparticle Synthesis and Characterization

Nanoformulations of the parent CAB (NCAB) and of its prodrugs (NMCAB, NM2CAB and NM3CAB) were manufactured by high-pressure homogenization using the poloxamer surfactant, 407 (P407). The drug/prodrug and P407 were premixed (10:1 w/w) in endotoxin free water for 24 hours in the concentration range of 2%-20% w/v drug/prodrug and 0.2-2% w/v P407. The premix was further homogenized using an Avestin EmulsiFlex-C3 high-pressure homogenizer (Ottawa, ON, Canada) at 18,000 psi to generate homogenous nanocrystals of desired particle size. Nanoparticles were characterized for particle size ($D_{eff}$), polydispersity index (PDI), and zeta potential by dynamic light scattering (DLS) using a Malvern Nano-ZS (Worcestershire, UK). The stability of the nanoformulations was monitored at 4, 25 and 37° C. over 3 months. Drug/prodrug content in nanoformulation was measured by dissolving the nanoformulation in methanol (Dilution factor range: 1000-10000), and analyzed by UPLC UV/Vis. Following equation was used to calculate encapsulation efficiency. Encapsulation efficiency (%)=(weight of drug in formulation/initial weight of drug added)×100. Morphology of nanoparticles was assessed by scanning electron microscopy (SEM). Nanoparticles were fixed in a solution of 2% glutaraldehyde, 2% paraformaldehyde in a 0.1 M sorenson's phosphate buffer (pH 7.2) at 4° C. for 24 hours and processed for imaging. Briefly, nanosuspensions were air dried onto a glass coverslip mounted on an SEM sample stub and sputter coated with approximately 50 nm of gold/palladium alloy. Samples were assayed using a FEI Quanta 200 scanning electron microscope (Hillsboro, Oreg.) operated at 5.0 kV (Sillman, et al., Nat. Commun. (2018) 9:443).

Human Monocytes Derived Macrophages (MDM)

Human monocytes were obtained by leukapheresis from HIV-1/2 and hepatitis B seronegative donors and later purified by counter-current centrifugal elutriation (Gendelman, et al., J. Exper. Med. (1988) 167:1428-1441). Monocytes were cultured in DMEM media containing 4.5 g/L glucose, L-glutamine, and sodium pyruvate supplemented with 10% heat-inactivated human serum, 50 µg/mL gentamicin, and 10 µg/mL ciprofloxacin. Cells were maintained at 37° C. in a 5% $CO_2$ incubator. Recombinant human macrophage colony stimulating factor (MCSF, 1000 U/mL) was added to culture media for first 7 days to facilitate monocyte-derived macrophages (MDMs) differentiation. Half-culture media was replaced with fresh media every other day. After differentiation, MDM were utilized for following in vitro assays.

Cytotoxicity Assay

Cellular viability following treatment with nanoparticles was evaluated by performing MTT assay. Human MDM plated in 96-well plates at a density of $0.08 \times 10^6$ cells per well were treated with 10, 25, 50, 100, 200, or 400 µM NCAB, NMCAB, NM2CAB or NM3CAB for 24 hours. Untreated cells were used as controls. For each group samples were in quadruplets. Cells were washed with PBS and incubated with 100 µL/well of MTT solution (5 mg/mL) for 45 minutes at 37° C. After incubation, MTT solution was removed, and cells were washed with PBS. Then, 200 µL of DMSO was added to each well, and absorbance was measured at 490 nm on a Molecular Devices SpectraMax® M3 plate reader with SoftMax Pro 6.2 software (Sunnyvale, Calif.).

Studies of Drug Particle MDM Uptake, Retention and Release

MDM uptake and retention studies were performed in clear flat-bottom 12-well plates at a density of $1.0 \times 10^6$ cells per well, with each treatment group completed in triplicate. For cellular uptake studies, MDM were treated with 100 µM NCAB, NMCAB, NM2CAB or NM3CAB. MDM were collected at 2, 4, 8 and 24 hours following treatment to measure intracellular drug and prodrug levels. For retention studies, MDM were treated with 100 µM of NCAB, NMCAB, NM2CAB, or NM3CAB for 8 hours, and then washed twice with phosphate buffered saline (PBS). Fresh culture medium was added and half-media was replaced every other day. MDM were collected at days 1, 5, 10, 15, 20, 25 and 30 to assay intracellular drug and prodrug concentrations. For both studies, at stated time points, adherent MDM were washed twice with PBS. Then cells were scraped into PBS, and counted using an Invitrogen Countess™ Automated Cell Counter (Carlsbad, Calif.). Cells suspension in PBS was centrifuged at 3,000 rpm for 8 minutes at 4° C. Obtained cell pellets were sonicated in 200 µL methanol using a probe sonicator to extract drug to extract intracellular drug. The resultants were centrifuged at 20,000 g for 10 minutes at 4° C. to separate cell debris from drug containing supernatant. Samples were further analyzed for drug and prodrug contents by UPLC-UV/Vis. For release studies, culture medium at the time points similar to those in the retention study was collected for quantitating the drug and prodrug released by MDM. The culture medium was mixed with methanol to precipitate the non-soluble components in the culture medium and to extract drug and prodrug. The mixture was centrifuged at 17,000 g for 10 minutes at 4° C. to separate the non-soluble precipitate. The supernatant was transferred to new tubes to be dried in speed vacuum. The dried contents were suspended in methanol for further analyzed by UPLC-UV/Vis.

Particle Characterization by Transmission Electron Microscopy (TEM)

MDM were treated with NCAB, NMCAB, NM2CAB or NM3CAB at concentration of 100 µM for 8 hours, and then washed twice with PBS. Fresh culture media were added and half-media was replaced every other day. MDM culture supernatant fluids were collected at days 0, 15, and 30 after drug-particle treatment, and analyzed by TEM to image intracellular nanoparticles. For day 0, cells were collected right after 8 hours treatment duration. At stated time points, cells were washed, scraped into PBS, pelleted at 3000 rpm for 8 minutes at room temperature, and fixed in a solution of 2% glutaraldehyde, 2% paraformaldehyde in 0.1 M Sorenson's phosphate buffer (pH 6.2). A drop of the fixed cell suspension was placed on a formvar/silicon monoxide 200 mesh copper grid and allowed to settle for 2 minutes. The excess solution wicked off and allowed to dry. A drop of NanoVan vanadium negative stain was placed on the grid for 1 minute, then wicked away and allowed to dry. Grids were examined on a FEI Tecnai G2 Spirit TWIN transmission electron microscope (Hillsboro, Oreg.) operated at 80 kV. Images were acquired digitally with an AMT digital imaging system (Woburn, Mass.) (Sillman, et al., Nat. Commun. (2018) 9:443).

HIV-1 Infection and Measurements of Reverse Transcriptase (RT) Activity in Infected Cell Fluids MDMs were plated in clear flat-bottom 24-well plates at a density of $0.8 \times 10^6$ cells/well. MDM were treated with 100 µM of NCAB, NMCAB, NM2CAB or NM3CAB for 8 hours. Following treatment, cells were washed with PBS and cultured in fresh culture medium with half-media replacement every other day. At 1, 5, 10, 15, 20, 25 and 30 days after the treatment, the cells were infected with HIV-1ADA (a macrophage tropic viral strain) at a multiplicity of infection (MOI) of 0.1 infectious particles per cell for 16 hours. Following infection period, MDM were washed with PBS and replenished with fresh media. Cells were cultured for next ten days with half-media replacement every other day, and the full media replacement on the 8th day. The culture media was collected on the 10th day after infection for the measurement of HIV-1 RT activity (Kalter, et al., J. Immunol. (1991) 146:3396-3404; Nowacek, et al., J. Neuroimmune Pharm. (2010) 5:592-601). The extent of infection was expressed as a percent of RT activity by infected MDM that were not treated. Cells were fixed in 2% PFA, and expression of HIV-1 p24 antigen was determined by immunocytochemistry (Nowacek, et al., J. Neuroimmune Pharm. (2010) 5:592-601).

Half-Maximum Effective Concentration ($EC_{50}$) Assay

MDM were plated in clear flat-bottom 96-well plates ($0.08 \times 10^6$ cells/well). Cells were treated with a range of drug concentrations, 0.01-1000 nM of CAB, MCAB, M2CAB, M3CAB, NCAB, NMCAB, NM2CAB, or NM3CAB for 1 hour prior to infection with HIV-1ADA (MOI of 0.1 infectious particles per cell) for 4 hours. After 4 hours of viral challenge, cells were washed and given fresh media containing drug (0.1-1000 nM). Subsequently, cell supernatants were collected 10 days later and assayed for HIV-1 RT activity as described above.

Nanoparticle Uptake in CD4+ T-Cells Using CEM-ss Cells as Standards

CEM-ss CD4+ T-cells were suspended in RPMI supplemented with 10% fetal bovine serum, 100 U/mL penicillin and 100 µg/mL streptomycin. Cell suspension (1 mL/well) was added in clear flat-bottom 12-well plates pre-coated with poly-L-lysine solution (500 µg/mL in distilled water) for 1 hour. After attachment to wells surface, cells were treated with 25 µM NCAB, NMCAB, NM2CAB or NM3CAB. At 2, 4 and 8 hours, cells were washed and scrapped into PBS. Cell suspension was centrifuged at 200 g for 5 minutes and intracellular drug and prodrug concentrations were quantified by Waters TQD mass spectrometer. Uptake of nanoparticles in CEM-ss CD4+ T-cell lines was confirmed by TEM imaging after 8 hours of treatment at 25 µM concentration. Sample processing for TEM imaging is described above.

Pharmacokinetics (PK) and Biodistribution (BD) Mouse Studies

NSG mice (Female, 6-8 weeks, Jackson Labs, Bar Harbor, Me.) were administered 45 mg/kg CAB-equivalents of NCAB, NMCAB, NM2CAB or NM3CAB by a single intramuscular (IM, caudal thigh muscle) injection at 40 µL/25 g mouse. Following injection, blood samples were collected into heparinized tubes at day 1 post-administration and then weekly up to day 364 by cheek puncture (submandibular vein, MEDIpoint, Inc., Mineola, N.Y.). Collected blood (25 µL) was immediately diluted into 1 mL ACN and stored at −80° C. until drug measurements. Remaining blood samples were centrifuged at 2,000 g for 8 minutes for plasma collection. Plasma was collected and stored at −80° C. for analysis of drug contents. At day 14, 28, 42 and 364 following administration, animals were humanly euthanized by isoflourane inhalation, followed by cervical dislocation. Spleen, lymph nodes, liver, lung, gut, kidney, brain, vaginal tissue, and rectal tissue were collected for quantitation of CAB and prodrug concentrations. CAB, MCAB, M2CAB and M3CAB were quantitated in mouse plasma, blood and tissues by UPLC-MS/MS using a Waters ACQUITY H-class UPLC (Waters, Milford, Mass., USA) connected to a Xevo TQ-S micro mass spectrometer. All solvents for sample processing and UPLC-MS/MS analysis were LCMS-grade (Fisher). For plasma and blood samples, 25 µL of sample was added into 1 mL acetonitrile (ACN) spiked with 10 µL internal standard (IS). d3-Dolutegravir (d3-DTG), myristoylated dolutegravir (MDTG), and stearoylated darunavir (SDRV), at a final concentration of 200, 20 and 20 ng/mL, respectively, were used as ISs for CAB, MCAB and M2CAB/M3CAB analyses, respectively. Samples were vortexed and centrifuged at 17,000×g for 10 minutes at 4° C. The supernatants were collected and dried using a SpeedVac® and reconstituted in 100 µL 80% methanol; 10 µL was injected for MCAB, M2CAB, and M3CAB UPLC-MS/MS analysis. Standard curves were prepared in blank mouse plasma/blood in the range of 0.2-2000 ng/mL for CAB, MCAB, M2CAB, and M3CAB. For tissue drug quantitation, 3-200 mg of sample was homogenized in 4-29 volumes of 0.1% v/v formic acid and 2.5 mM ammonium formate containing 90% methanol. To 100 µL of tissue homogenate was added 280 µl methanol containing 0.1% formic acid and 2.5 mM ammonium formate, 80% methanol (10 µL), and IS (10 µL), followed by vortexing for 3 min and centrifugation at 17,000×g for 15 minutes. For MCAB, M2CAB and M3CAB analyses, 85 µl of supernatant was mixed with 15 µl water. For CAB analysis, 20 µl of supernatant was mixed with 80 µl of 50% ACN. These aliquots were vortexed, centrifuged at 17,000×g for 10 minutes and 10 µl of supernatant was used for LC-MS/MS analysis. Standards were prepared similarly using blank tissue homogenates with 10 µL of spiking solution (CAB/MCAB/M2CAB/M3CAB, 5-20,000 ng/mL in 50% ACN). For CAB quantitation, chromatographic separation of 10 µL CAB sample was performed on a Waters ACQUITY UPLC BEH Shield RP18 column (1.7 µm, 2.1 mm×100 mm) using a 10-minute gradient of mobile phase A (7.5 mM ammonium formate in water, adjusted to pH 3 using formic acid) and mobile phase B (100% ACN) at a flow rate of 0.25 mL/minute. For the first 3.5 min, the mobile phase composition was 35% B and was increased to 95% B in 0.5 min and held constant for 1.5 minute. Mobile phase B was then reset to 35% in 0.5 min and the column was equilibrated for 1 minute before the next injection. For MCAB and M2CAB quantitation chromatographic separation was achieved on a shorter 30 mm column (PN with an 8-min gradient method at a flow rate of 0.28 mL/minute. The initial mobile phase composition was 80% B for the first 2 min, and increased to 95% B in 4 minutes, held constant for 0.75 minute, reset to 80% in 0.25 minute and the column was equilibrated for 1 minute before the next injection. For M3CAB quantitation chromatographic separation was achieved also on a shorter 30 mm column with an 8-minute gradient method at a flow rate of 0.35 mL/min. The initial mobile phase composition was 88% B for the first 5 min, and increased to 95% B in 0.25 min, held constant for 1.5 minutes, reset to 88% in 0.25 minute and the column was equilibrated for 1 minute before the next injection. CAB, MCAB, M2CAB, and M3CAB were detected at a cone voltage of 10 V, 24 V, 2 V and 20 V respectively, and a collision energy of 24 V, 18 V, 24 V and 26 V respectively, in the positive ionization mode. Multiple reaction monitoring (MRM) transitions used for CAB, MCAB, M2CAB, M3CAB, d3-DTG, MDTG and SDRV were 406.04>126.93, 616.28>406.09, 672.34>406.07, 728.47>406.09, 422.84>129.99, 630.20>420.07 and 814.52>658.44, respectively. Spectra were analyzed and quantified by MassLynx software version 4.1. All quantitations were determined using analyte peak area to internal standard peak area ratios. Following PK and BD analysis in NSG mice, superior NM2CAB, among all formulations, was again evaluated in another strain of mice, BALB/cJ. (Male, 6-8 weeks, Jackson Labs). NCAB was used as a control. Mice injected with NM2CAB were humanly euthanized at day 280 following administration. Drug and prodrug quantitation in collected plasma and tissue was similar to above. Non-compartmental PK analysis for plasma CAB was performed using Phoenix WinNonlin-8.0 (Certara, Princeton, N.J.) for studies in NSG mice.

PK and BD in rhesus monkeys (RM)

Four male RMs (4.4-6.7 kg; PrimeGen) were anesthetized with ketamine (10 mg/kg) and subsequently administered 45 mg/kg CAB-eq. of NM2CAB and a lab-generated RPV prodrug by IM injection (quadriceps femoris muscle, 0.5 mL/kg). Blood samples were collected in potassium-EDTA coated tubes for complete blood counts (CBC), metabolic profiles. Plasma was separated for drug measurements. Tissue biopsies of lymph node, adipose and rectal tissues were collected at day 204 after injection for drug quantitation. Quantitation methods for drug and prodrug in plasma and tissues were similar to described above in mice studies.

Statistical Analyses

Statistical analysis were made using GraphPad Prism 7.0 software (La Jolla, Calif.). Data of in vitro studies were expressed as mean±SEM with a minimum of 3 biological replicates, while in vivo study results were expressed as mean±SEM with a minimum of 3 biological replicates. For comparisons between two groups, Student's t test (two-tailed) was used. A one-way ANOVA followed by a Tukey's test was used to compare three or more groups. Statistical significances were denoted as follows: *$P<0.05$, $P<0.01$, *$P<0.001$, ****$P<0.0001$.

Study Approvals

All animal studies were approved by the University of Nebraska Medical Center Institutional Animal Care and Use Committee (IACUC) in accordance with the standards incorporated in the Guide of the Care and Use of Laboratory Animals (National Research Council of the National Academies, 2011). Human monocytes were isolated by leukopheresis from HIV-1/2 and hepatitis B seronegative donors according to an approved UNMC Institutional Review Board exempt protocol.

Results

Prodrug Synthesis and Characterization

CAB was chemically modified by attaching fatty acid chains of variable carbon lengths-14, 18, and 22, to produce esters MCAB, M2CAB, and M3CAB respectively. The prodrugs were further characterized by nuclear magnetic resonance (NMR) to confirm the synthesis. $^1$H NMR spectra of all three prodrugs showed triplets in the range of 0.86-0.89, 1.77-1.78 and 2.66-2.70 ppm and a broad singlet in the range of 1.24-1.25 ppm corresponding to the terminal methyl and repeating methylene protons of the fatty acid alkyl chain. Disappearance of the phenol proton peak at 11.5 ppm confirmed the substitution of CAB's hydroxyl proton with fatty acyl moieties. $^{13}$C NMR spectrum of each prodrug confirmed the carbon atoms of the conjugated aliphatic chain. Electrospray ionisation mass spectrometry (ESI-MS) affirmed the molecular weights of all prodrugs. ESI-MS infusion for MCAB generated a strong signal at 616.28 m/z, ESI-MS infusion for M2CAB generated a strong signal at 672.34 m/z, and ESI-MS infusion for M3CAB generated a strong signal at 728.47 m/z. Fourier transform infrared spectroscopy (FTIR) prodrug characterization produced bands not observed for CAB in the ranges of 2908-2935 and 1748-1775 cm$^{-1}$. These correspond to C—H stretches in aliphatic methylene groups and C=O stretch corresponding to carboxyl group in ester bond, respectively. XRD spectra over $2\theta=2\text{-}70°$ showed the crystalline character of prodrugs MCAB, M2CAB and M3CAB. Nanoparticles of M2CAB maintained the crystalline property of prodrug. A significant serial reduction in the aqueous solubility of MCAB (2.83±1.37 µg/mL), M2CAB (1.91±0.23 µg/mL) and M3CAB (1.51±0.7 µg/mL) was observed compared to CAB (12.12±0.41 µg/mL). Moreover, compared to CAB (0.09±0.002 mg/mL), a parallel significant increase in 1-octanol solubility of MCAB (2.31±28.15 mg/mL), M2CAB (2.64±0.02 mg/mL) and M3CAB was observed. These results confirmed the increase in the hydrophobicity and lipophilicity of the prodrugs compared to CAB as a result of chemical modifications with the fatty acid conjugates.

Prodrugs are pharmacologically inactive compounds that require enzymatic or hydrolytic activation for bioconversion into active drugs in physiological conditions. Therefore, hydrolysis kinetics of MCAB, M2CAB and M3CAB and subsequent CAB formation were evaluated in plasma of different species (mouse, rat, rabbit, monkey, dog, and human). Upon incubation in plasma of all the species tested, MCAB showed more than 85% cleavage within 30 minutes, M2CAB showed an average of 75% cleavage by 2 hours and 80% cleavage by 6 hours. M3CAB showed the slowest rate of cleavage with around 50% prodrug remaining after 24 hours of incubation in plasma. These studies showed that MCAB rapidly converted into CAB while M3CAB showed the least conversion into CAB. CAB formation from M2CAB hydrolysis was an average 71.1% by 6 hours, signifying that M2CAB is the optimal prodrug in terms of stability and active drug formation in physiological conditions. There were some differences in rates of prodrug hydrolysis among plasma of various animal species. The variability in the plasma CAB concentrations amongst the tested species can be the result of differences in body fat distribution, muscles mass, physical activity and in plasma carboxylesterases enzymes operative for prodrug hydrolysis (Trezza, et al., Curr. Opin. HIV AIDS (2015) 10:239-245; Bahar, et al. (2012) J. Pharm. Sci. (2012) 101:3979-3988; Wang, et al., Acta Pharmaceutica Sinica. B (2018) 8:699-712). Moreover, chemical stability of M2CAB was determined at room temperature and elevated temperature (37° C.) in acidic (pH 1), neutral (pH 7), and basic conditions (pH 11) over 24 hours to determine the long-term stability of prodrug nanoformulations at various storage conditions. At room temperature, at 24 hours, 19% hydrolysis in acidic conditions, and 24% hydrolysis in neutral conditions were determined. However, at basic conditions M2CAB was completely hydrolyzed and was undetected. At 37° C., at 24 hours, around >95% prodrug was hydrolyzed in acidic conditions and 28% prodrug was hydrolyzed in neutral conditions. Whereas, at basic conditions M2CAB was completely hydrolyzed within 2 hours. The half-maximum effective concentration ($EC_{50}$) values of the prodrugs, MCAB, M2CAB and M3CAB, were compared with CAB to determine the changes, if any, in antiretroviral activity due to chemical modification. HIV-1 RT activity measurements of the culture medium of MDM infected with HIV-1$_{ADA}$ demonstrated that the $EC_{50}$ values of CAB (28.39 nM), MCAB (34.19 nM), M2CAB (44.71 nM), and M3CAB (51.15 nM) were comparative, indicating no significant effect on drug activity.

Nanoformulation Manufacture and Characterization

Nanoformulations of CAB (NCAB), MCAB (NMCAB), M2CAB (NM2CAB) and M3CAB (NM3CAB) were manufactured by top down synthesis utilizing high-pressure homogenization. The encapsulation efficiency of drug or any of prodrug was >85%. Poloxamer 407 (P407) surfactant provided particle surface stabilization. Nanoparticle size, polydispersity index (PDI), and zeta potential were determined by DLS at room temperature (RT), 4° C., and 37° C.

All the formulations remained stable up to 98 days, signifying that these formulations can maintain their physical integrity at a range of storage conditions. Moreover, temperature variation did not affect the physicochemical properties of any formulation over the period of study. At the day of manufacture, average particle size, PDI and zeta potential for NCAB were 294.5±1.8 nm, 0.23±0.01, −28.3±0.21 mV; for NMCAB were 302.1±10.8 nm, 0.23±0.01, −31.1±1.1 mV; for NM2CAB were 359.7±3.63 nm, 0.23±0.02, −31.3±0.1 mV; and for NM3CAB were 268.47±6.9 nm, 0.23±0.03, −31.1±0.06 mV. At day 98 post-manufacture, physicochemical parameters for NCAB were 327.5±4.9 nm, 0.21±0.04, −18.2±0.25 mV; for NMCAB were 388.7±6.4 nm, 0.22±0.03, −24.8±2.87 mV; for NM2CAB were 369.5±2.5 nm, 0.19±0.03, −19.6±0.53 mV; and for NM3CAB were 245.6±2.6 nm, 0.27±0.06, −25.7±0.56 mV. The SEM images showed that NCAB, NMCAB, NM2CAB and NM3CAB nanoparticles had uniform rod-shaped morphology. For conformation of reproducibility, the NM2CAB formulation was manufactured in 11 separate batches (Table 1). Nanoparticle sizes varied from 243.00±2.48 to 378.00±1.90 nm with a narrow PDI (0.18±0.03 to 0.33±0.03).

TABLE 1

Reproducibility of NM2CAB synthesis

| Manufacture Batch no. | Size ± SEM (nm) | Pdl ± SEM |
|---|---|---|
| 1 | 320.13 ± 6.81 | 0.23 ± 0.02 |
| 2 | 322.10 ± 2.99 | 0.21 ± 0.01 |
| 3 | 328.67 ± 1.60 | 0.18 ± 0.03 |
| 4 | 311.43 ± 4.53 | 0.33 ± 0.03 |
| 5 | 287.17 ± 0.94 | 0.22 ± 0.01 |
| 6 | 317.57 ± 2.83 | 0.27 ± 0.01 |
| 7 | 378.00 ± 1.90 | 0.26 ± 0.01 |
| 8 | 244.63 ± 5.85 | 0.19 ± 0.01 |
| 9 | 268.97 ± 7.66 | 0.19 ± 0.02 |
| 10 | 259.77 ± 2.09 | 0.23 ± 0.01 |
| 11 | 243.00 ± 2.48 | 0.22 ± 0.01 |

The effect of nanoformulations on antiretroviral activity of prodrugs ($EC_{50}$) was determined. Antiviral activity of NCAB, NMCAB, NM2CAB, or NM3CAB was determined in MDM at a range of concentrations (0.01-1000 nM) and measured by HIV-1 reverse transcriptase activity after viral challenge with HIV-1ADA at an MOI of 0.1. $EC_{50}$ values were increased compared to non-nanoformulated drug or prodrugs, likely due to the required dissolution of nanoparticles prior to cleavage of prodrugs. $EC_{50}$ values were comparable among NCAB (39.83 nM), NMCAB (89.67 nM), NM2CAB (37.02 nM). However, the $EC_{50}$ value for NM3CAB was increased significantly (~1.78E+06 nM). This could be an effect of slower cleavage of prodrug and subsequent generation of active CAB as well as of intracellular stability of nanoformulations. For the further characterization of prodrug nanoformulations and determination of the treatment concentrations for in vitro studies, the cellular vitality was assessed in MDM and CEM-ss CD4+ T-cells by MTT assay. In MDM, no cytotoxicity was seen at the tested range of concentrations (10-400 µM) for all nanoformulations. In CEM-ss CD4+ T-cells, cytotoxicity was determined at 50 µM and above concentrations. Therefore, treatment concentrations for all nanoformulations were 100 µM for assays in MDM and 25 µM for studies in CEM-ss CD4+ T-cells.

In Vitro Screening in MDM and CEM-Ss CD4+ T Cells

Macrophages can be successfully utilized as cellular drug depots and carriers. Because of their phagocytic nature and the ability to migrate throughout the body (Zhou, et al., Biomaterials (2018) 151:53-65; Darville, et al., J. Pharm. Sci. (2014) 103:2072-2087; Aderem, et al., Ann. Rev. Immunol. (1999) 17:593-623; Dou, et al., Blood (2006) 108:2827-2835), MDM can serve as drug delivery systems to viral reservoirs. Therefore, MDM were used as in vitro system to evaluate the nanoformulations (Zhou, et al., Biomaterials (2018) 151:53-65; Hilaire, et al., J. Control Release (2019) 311-312:201-211; Ibrahim, et al., Int. J. Nanomedicine (2019) 14:6231-6247; Lin, et al., Chem. Commun. (2018) 54:8371-8374; Sillman, et al., Nat. Commun. (2018) 9:443; Smith, et al., Biomaterials (2019) 223:119476; Soni, et al., Biomaterials (2019) 222:119441).

Uptake assay was performed in MDM by measuring drug and prodrug levels following treatment with 100 µM NCAB, NMCAB, NM2CAB or NM3CAB up to 24 hours. Intracellular prodrug levels measured for NMCAB, NM2CAB and NM3CAB were 61.69±0.78, 84.07±5.82, and 73.34±13.59 nmoles/$10^6$ cells, respectively by 24 hours; and intracellular CAB levels were 0.58±0.11, 12.31±0.46, 17.79±2.92, and 7.97±1.76 nmoles/$10^6$ cells for NCAB, NMCAB, NM2CAB or NM3CAB, respectively. Afterwards, the capacity of macrophages to retain intracellular drug and prodrug was evaluated over a period of 30 days following single treatment. MDM were treated with 100 µM NCAB, NMCAB, NM2CAB or NM3CAB for 8 hours. Intracellular prodrug levels were sustained up to 30 days following single treatment. Specifically, the amount of intracellular prodrug measured at day 30 for NMCAB, NM2CAB and NM3CAB were 0.41±0.09, 14.21±2.28, and 26.70±3.29 nmoles/$10^6$ cells. Similarly, intracellular CAB levels formed from prodrug cleavage were measured up to 30 days. The amount of intracellular CAB levels measured at day 30 for NM2CAB and NM3CAB were 1.71±0.35 and 2.05±0.10 nmoles/$10^6$ cells. Whereas, intracellular CAB levels fell below the limit of quantitation within 24 hours after NCAB treatment; and intracellular CAB concentration following NMCAB treatment was measured up to day 25 (0.09±0.04 nmoles/$10^6$ cells), and was undetectable at day 30. In parallel to retention assay, CAB released into culture fluids were measured over 30 days. NM2CAB showed the most sustained CAB release with drug levels of 1.0±0.10 nmoles/$10^6$ cells at day 30. No CAB was detected with NCAB and NM3CAB treatment. Prodrugs were not detected in culture medium for any of the treatment, indicating prodrug bioconversion.

Next, TEM images of MDM were taken at day 0, 15, 30 after treatment with nanoformulations for 8 hours to assess the presence of nanoparticles in the cytoplasmic vesicles. TEM images confirmed the presence of prodrug nanoformulations (NM2CAB and NM3CAB) up to day 30 in MDM, signifying the drug-depot property of MDM; and validated the uptake, retention and release results. Uptake of NCAB, NMCAB, NM2CAB or NM3CAB was determined in CD4+ T-cells following treatment at 25 µM concentration reflected what was observed in MDM. TEM imaging performed on CEM-ss CD4+ T-cells following single treatment of NCAB, NMCAB, NM2CAB or NM3CAB for 8 hours confirmed the presence of nanoparticles in cytoplasmic compartments.

To examine whether sustained drug retention in MDM would protect against HIV-1 infection, cells were challenged with HIV-1ADA up to 30 days following an 8-hour treatment with 100 µM NCAB, NMCAB, NM2CAB and assayed quantitatively for HIV-1 RT activity, as well as qualitatively for HIV-1 p24 antigen expression. NM3CAB was not selected for this study as it did not show significant protection at the desired $EC_{50}$ value. NM2CAB treatment suppressed HIV-1 RT activity up to day 30 and was confirmed by absence of HIV-1 p24 expression. In contrast, complete viral breakthrough occurred at day 1 post-NCAB treatment and at day 20 post-NMCAB treatment. Therefore, enhanced MDM drug retention exhibited by NM2CAB provided superior protection against HIV-1 challenge compared to NACB and NMCAB. In addition, dose response antiretroviral activity of NM2CAB was determined (FIG. 4). MDM were treated with 10, 50 or 100 µM NM2CAB for 8 hours and challenged with HIV-1ADA. Similar to above, antiretroviral activity was determined up to 30 days. A complete viral suppression was observed in 50 and 100 µM NM2CAB treatments while 57% protection was seen in 10 µM treatment after 30 days and validated by HIV-1 p24 expression (FIG. 4).

Pharmacokinetics (PK) and Biodistribution

To assess PK and biodistribution profiles, female NSG mice were injected IM with single dose of 45 mg/kg CAB-equivalents of NCAB or NMCAB or NM2CAB. Immunodeficient female NSG mice were used for evaluation to mimic disease pathology of immune compensation and to assess biodistribution in genitourinary tracks. NCAB is an effective equivalent formulation to CAB-LA as both formulations yielded similar plasma CAB levels up to day 49 after administration to BALB/cJ mice.

At day 1 post-injection, NCAB treatment generated higher plasma CAB concentrations compared to both NMCAB and NM2CAB and showed faster decay kinetics over the study period in comparison to NM2CAB. With NCAB treatment, plasma CAB concentrations were maintained above the four times protein-adjusted 90% inhibitory concentration ($4 \times PA\text{-}IC_{90}$; 664 ng/mL) up to day 35 (792.7 ng/mL), then rapidly declined to below the $PA\text{-}IC_{90}$ (166 ng/mL) by day 49 (75 ng/mL) before falling below the limit of quantitation (0.5 ng/mL) by day 126. NMCAB treatment showed slower decay, and maintained plasma CAB levels above the $4 \times PA\text{-}IC_{90}$ up to day 91 (673.8 ng/mL) and above $PA\text{-}IC_{90}$ up to day 168 (186.7 ng/mL). At day 364 post-NMCAB treatment, CAB levels were quantified at 8.5 ng/mL. In stark contrast, NM2CAB treatment provided slower plasma decay kinetics compared to both NCAB and NMCAB up to day 364, maintaining sustained plasma CAB concentration above the $4 \times PA\text{-}IC_{90}$ up to day 231 (702 ng/mL) and above the $PA\text{-}IC_{90}$ up to day 364 (354.2 ng/mL). Plasma pharmacokinetic parameters for CAB were determined using noncompartmental analysis for all treatment groups. Quantitation of PK parameters demonstrated that apparent CAB half-life following NM2CAB (131.56 days) treatment was 17- and 3-fold greater than those of NCAB (7.80 days) and NMCAB (44.40 days), respectively. Similarly, CAB mean residence time (MRT) of NM2CAB was 21-fold longer than NCAB (201.94 vs. 9.79 days, respectively) and 7-fold longer than NMCAB (201.94 day vs. 30.76 day, respectively).

NM2CAB also elicited significantly higher CAB tissue levels for up to a year. Tissue biodistribution of CAB was assessed at day 14, 28, 42 and 364 after single IM injection in vaginal tissue, rectal tissue, spleen, liver, gut, brain, kidney, lung, and lymph nodes-anatomical associated tissues. Drug levels in lymph nodes were determined in anatomical regions associated with lymph nodes only at day 28 and 364, due their immature state in immunodeficient NSG mice. Notably, MCAB levels were lower than M2CAB at day 14, 28 and 42 and were undetectable at day 364. For NM2CAB, at day 364, prodrug levels were 3414.8 ng/g (spleen), 909.8 ng/g (liver), 52.7 ng/g (lung), 50.3 ng/g (brain), 3.9 ng/g (kidney) and 18710.1 ng/g (lymph nodes). At day 28, CAB levels in all tissues were comparable between NCAB and NM2CAB. However, by day 42, CAB levels in all tissues tested after NCAB treatment were significantly lower compared to those after NM2CAB treatment (vaginal tissue, spleen, gut, brain, kidneys and lungs rectal tissue and brain). Whereas, CAB levels in tissues, up to day 42, following NMCAB treatment were significantly higher compared to NCAB and NM2CAB treatments. At day 364 following treatment with NM2CAB, CAB concentrations were significantly higher in all tested tissues compared to other formulations, and CAB levels were measured at 27 ng/g (vaginal tissue), 19.7 ng/g (rectum), 41.1 ng/g (spleen), 67.62 ng/g (lymph nodes-anatomical associated tissues), 123.9 ng/g (liver), 10.3 ng/g (gut), 7.5 ng/g (brain), 33.2 ng/g (kidney) and 35.5 ng/g (lung). In contrast, CAB levels were significantly low or below the limit of quantitation (0.5 ng/g) in all tissues at day 364 after treatment with NCAB or NMCAB.

Prodrug (MCAB or M2CAB) concentrations in blood and all tissues was also tested (FIG. 5). Concentrations of both prodrugs in blood were lower at day 1 post-injection, 22 ng/mL for MCAB and 31.3 ng/mL for M2CAB, and rapidly went blow the limit of quantitation, signifying bioconversion of prodrugs to active parent drug. All the screened tissues were substantial depots for M2CAB and had sustained levels of M2CAB throughout the study period. Single IM injection of NM3CAB (45 mg/kg CAB-equivalents) in female NSG mice generated low levels of plasma CAB (2248 ng/mL) at day 1-post administration compared to NCAB (41237.6 ng/mL), NMCAB (30148.9 ng/mL) and NM2CAB (7076.1 ng/mL). Plasma CAB levels reached around $PA\text{-}IC_{90}$ (233.2 ng/mL) within 28 days after treatment. Plasma and tissue levels of CAB and M3CAB were measured at day 28. For validation of slower hydrolysis of M3CAB, PK evaluation was repeated in BALB/cJ mice following single IM injection of NM3CAB at same dosage. Similar to PK results in NSG mice, NM3CAB generated low levels of plasma CAB at day 1-post administration (777.8 ng/mL); and plasma CAB levels fell down below the one-time $PA\text{-}IC_{90}$ within 28 days (98.9 ng/mL). These data confirmed the slower prodrug hydrolysis of M3CAB prodrug and subsequent bioconversion into the CAB.

Superior PK and BD profiles of NM2CAB among all formulations were confirmed in another strain of mice, BALB/cJ (male). Here, wild type mice were used to validate the results from immunodeficient NSG mice. PK and BD measurements in plasma and tissues for NM2CAB were parallel to those in NSG mice. Particularly, plasma CAB concentrations were above $PA\text{-}IC_{90}$ by day 231 (170.8 ng/mL) for NM2CAB, affirming the improvement in drug apparent half-life. NCAB was used as a control, in which CAB levels went below $PA\text{-}IC_{90}$ by day 28 (12.28 ng/mL).

To validate the results seen in rodents, rhesus macaques were injected IM with single dose of 45 mg/kg CAB-equivalents of NM2CAB. Plasma CAB and prodrug (M2CAB) levels were measured up to day 393. Similar to results in mice, NM2CAB treatment provided slower plasma decay kinetics, maintaining sustained plasma CAB concentration up to day 393. At day 393, CAB levels were measured at an average of 56.1 ng/mL. As expected, plasma M2CAB concentrations were lower throughout the study compared to CAB levels, signifying the bioconversion of prodrug to its active parent drug (FIG. 6A). Rectal, lymph node, and adipose tissue biopsies were collected at day 204 following NM2CAB administration and analyzed for CAB and M2CAB levels. CAB concentrations in the rectal, lymph node and adipose tissues were 10.12 ng/g, 22.7 ng/g and 29.5 ng/g, respectively (FIG. 6B). M2CAB was present at high levels in lymph node and adipose tissues (33.3 ng/g and 233.2 ng/g, respectively), with lower levels (1.7 ng/g) in rectal tissue (FIG. 6C).

Toxicity Evaluation

Post-NM2CAB administration, toxicological assays were performed in both mice and rhesus macaques. For toxicity assessment in NSG mice, animal weights were recorded weekly for a year; and at the study conclusion (day 364), plasma and tissues were collected for metabolic profiles and histopathology, respectively. Age matched untreated mice were used as controls. No differences in weights were observed among animals from all groups. Comprehensive serum chemistry parameters were quantified using a VetScan comprehensive diagnostic profile disc and a VetScan VS-2 instrument. Examined parameters were (alanine aminotransferase (ALT), albumin (ALB), alkaline phosphatase (ALP), amylase (AMY) total calcium (CA++), creatinine (CRE), globulin (GLOB), glucose (GLU), phosphorus (PHOS), potassium (K+), sodium (NA+), total bilirubin (TBIL), total protein (TP), and urea nitrogen (BUN). No significant differences were noted between controls and NM2CAB treated groups indicating that NM2CAB did not adversely affect functions of systemic organs. Histological examination of tissue sections (liver, lung, gut, spleen, kidney and brain) stained with H&E by a certified pathologist revealed no abnormal pathology in NM2CAB treated animals. Moreover, the formulation was well tolerated by both strains of mice (NSG and BALB/cJ), and no injection site reactions and changes in behavior or movement were observed.

For assessment in rhesus macaques, weights were recorded starting from pre-administration of formulation, and plasma and peripheral blood mononuclear cells (PBMCs) were collected for complete blood counts and metabolic profiles up to day 393 post-NM2CAB administration. Systemic toxicity was evaluated by measuring both hematologic (neutrophil, lymphocyte, monocyte) and metabolic (ALT, alkaline phosphatase, BUN/creatinine) profiles. No weight changes were recorded in any of the animals following injection. An initial mild redness observed at the site of injection was resolved by day 3 in all animals. No inflammation or bolus was noted 3 days after injection. Neutrophils, lymphocytes and monocytes were counted prior to-and post-NM2CAB administration; and the count of blood cells was consistent. At day 1 post-injection an increase in neutrophil count was recorded, and it became normal within 2 weeks in all animals. Such a change could be related to injection and may not be drug associated. Liver and kidney metabolic profiles were unchanged in all animals following treatment. Overall, no adverse events were observed after NM2CAB administration.

Drug-Drug Interactions

Drug-drug interaction were evaluated between two prodrug nanoformulations (NM2CAB and NM3PRV) of drugs of different classes: CAB (INSTIs) and rilpivirine (RPV; NNRTI). RPV was a choice of drug along with CAB due to current clinical development of combination of long-acting CAB and RPV nanoformulations. NM3RPV is a long-acting formulation of RPV (Hilaire, et al., J. Control Release (2019) 311-312:201-211). BALB/cJ mice were treated IM with a single dose of NM2CAB alone (45 mg/kg CAB-equivalents), NM3RPV alone (45 mg/kg RPV-equivalents) or co-administration of both prodrug nanoformulations (NM2CAB and NM3RPV, 45 mg/kg drug-equivalents). Plasma levels of CAB and RPV were measured, and no differences in active drug levels were observed between animals treated with formulations alone or in combination, signifying usage of combination of multiple prodrug nanoformulations for treatment or prevention.

With an inability to eradicate HIV infection protective vaccines and pre-exposure prophylaxis (PrEP) for persons at risk, long-term ART are the sole approaches available to prevent disease and halt new infections and viral transmission. This is highlighted by 'treatment as prevention' for those people at risk of infection. The focus in developing LA ARV injectables center on creating drugs with long-half lives. For PrEP, LA ARVs require "coverage" to preclude infections after HIV exposures. Viral infection need be halted during time periods where protective ARV levels are detected in plasma. The drugs must also be given without untoward side effects that include gastrointestinal toxicity and any notable drug-drug interactions. Currently, LA agents have received enthusiasm amongst potential users with the potential advantages of eliminating the stigma of viral infections and by requiring less-than-daily dosing intervals, some dosed as infrequently as every 2 to 3 months. LA ARVs administered by subcutaneous or intramuscular routes are highly effective and have already demonstrated enhanced life quality and longevity (May, et al., AIDS (2014) 28:1193-1202; Antiretroviral Therapy Cohort, Lancet (2017) HIV 4:e349-e356). They help circumvent the lack of adherence to medication which remains as a key treatment challenge (Shubber, et al., PLoS Med. (2016) 13:e1002183; Osterberg, et al., New Eng. J. Med. (2005) 353:487-497). Indeed, any poor compliance to ARV regimens resulting in treatment failure, drug-resistant mutations, and new viral transmissions can be eliminated with improved adherence. In attempts to improve upon existing platforms for LA ARVs, long acting slow effective release antiretroviral therapy (LASER ART) prodrugs have been developed. These new formulations serve to reduce frequency of injections while maintaining the sustained therapeutic levels of ARVs for longer duration (Edagwa, et al., Exp. Opinion Drug Del. (2017) 14:1281-1291). LASER ART comprises prodrug synthesis through chemical modifications of existing ARV to provide slow native drug dissolution, poor water solubility, enhanced penetrance though biological membranes of cell as well as tissue reservoirs, and limited systemic off target toxicities. Prodrug synthesis allows the formation of ARV nanocrystals stabilized by polymer excipients. PK and efficacy (PD) of LASER ART formulations has been established for a range of ARVs including, but not limited, to dolutegravir (DTG), CAB, abacavir (ABC), lamivudine (3TC) and emtricitabine (FTC) (Zhou, et al., Biomaterials (2018) 151:53-65; Hilaire, et al., J. Control Release (2019) 311-312:201-211; Ibrahim, et al., Int. J. Nanomed. (2019) 14:6231-6247; Lin, et al., Chem. Commun. (2018) 54:8371-8374; McMillan, et al., Antimicrob. Agents Chemother. (2018) 62: e01316-17; McMillan, et al., AIDS (2019) 33:585-588; Sillman, et al., Nat. Commun. (2018) 9:443; Smith, et al., Biomaterials (2019) 223:119476; Soni, et al., Biomaterials (2019) 222: 119441).

CAB is an HIV-1 integrase strand transfer inhibitor (INSTI), and is currently is being developed as both oral and LA injectable (McPherson, et al., Expert Opin. Investig. Drugs (2018) 27:413-420). Its unique intrinsic properties, such as hydrophobic nature, long systemic half-life (approximately 40 hours after oral administration), high potency, resistant profile, low daily oral dosing requirement (<30 mg/day), and limited drug-drug interactions, make it an attractive candidate to develop into a LA injectable (Trezza, et al., Curr. Opin. HIV AIDS (2015) 10:239-245). Herein, it is demonstrated that a single injection of NM2CAB generated unexpectedly superior improvements in drug durability reflective by sustained drug plasma concentrations and tissue biodistribution compared against either NCAB, NMCAB, or NM3CAB. NM2CAB provided sustained plasma decay while maintaining drug levels above the PA-IC$_{90}$ of 166 ng/mL for 364 days following single injection.

CAB LA, currently nearing clinical approvals, was studied extensively in rhesus macaques affirming its abilities for use as an ARV injectable for pre-exposure prophylaxis (PrEP) studies (Edagwa, et al., Exp. Opin. Drug Del. (2017) 14:1281-1291; Stellbrink, et al., Curr. Opin. HIV AIDS (2018) 13:334-340). These studies demonstrated that CAB LA provided high extent of protection against vaginal, rectal, intravenous and penile challenges with SHIV strains supporting its future use as for PrEP those people at high-risk of HIV exposure and for intravenous drug users. Plasma levels above 3×PA-IC$_{90}$ provided 100% protection and concentrations above PA-IC$_{90}$ provided 97% protection against viral challenge (Edagwa, et al., Exp. Opin. Drug Del. (2017) 14:1281-1291; Stellbrink, et al., Curr. Opin. HIV AIDS (2018) 13:334-340). Herein, NM2CAB administration generated plasma CAB concentrations above PA-IC$_{90}$ for more than six months signifying its superiority and its clinically efficacy as PrEP.

In all, the development of effective antiretroviral drug (ARV) treatment and prevention measures for HIV-1-infected patients has changed from what was certain death to a manageable life-long chronic ailment. The need for the control of the HIV-1 pandemic remains as an estimated 37.9 people are infected worldwide. The advent of LA ARVs will certainly expand options for overcoming the challenge of suboptimal drug adherence and reduce the burden of HIV infection. To date, chemoprophylaxis with HIV antiretroviral agents has been demonstrated in largest measure with Tenofovir disoproxil fumarate (TDF)-containing compounds. However, required levels of adherence to daily or near-daily oral tablets has proven challenging. LA preparations offer greater choice for achieving prevention with the understanding that safety, tolerability and efficacy will continue to be part of the therapeutic outcome assessments. LA ARVs capable of being administered on a monthly or less frequent basis will improve therapeutic adherence and extend opportunities for PrEP.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A compound of formula I:

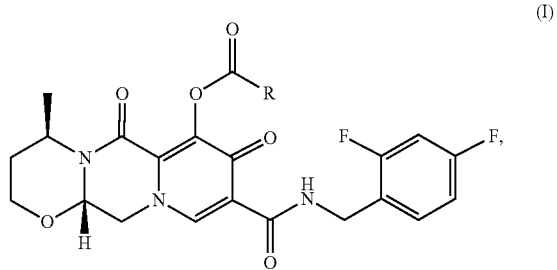

or a pharmaceutically acceptable salt thereof, wherein R is a saturated linear aliphatic chain of a length of 17 carbons.

2. A nanoparticle, comprising a compound of claim 1 and a polymer or surfactant.

3. The nanoparticle of claim 2, wherein said compound is

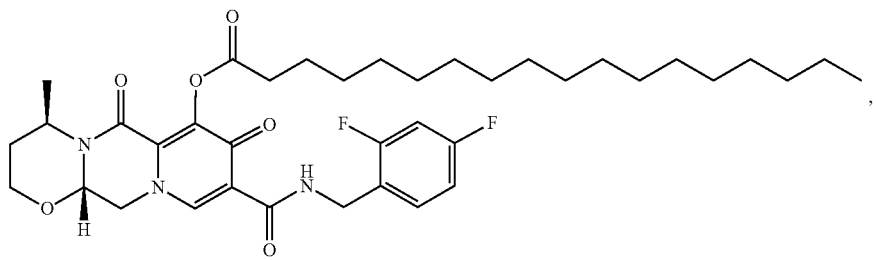 [SMILES: CCCCCCCCCCCCCCCCCC(=O)Oc1c2n(cc(C(=O)NCc3ccc(F)cc3F)c1=O)C[C@@H]1OCC[C@@H](C)N1C2=O]

or a pharmaceutically acceptable salt thereof, and the polymer or surfactant is P407.

4. A pharmaceutical composition, comprising a compound of claim 1, and a pharmaceutically acceptable carrier.

5. A method of treating an HIV infection in a subject in need thereof, wherein said method comprises administering to said subject a therapeutically effective amount a pharmaceutical composition of claim 4.

6. The method of claim 5, wherein the pharmaceutical composition is administered via injection.

7. The method of claim 5, wherein the pharmaceutical composition is administered one time in a 3, 6, 9, 12, 18, or 24 month period.

* * * * *

UNITED STATES PATENT AND TRADEMARK OFFICE
CERTIFICATE OF CORRECTION

PATENT NO. : 11,154,557 B2
APPLICATION NO. : 17/301030
DATED : October 26, 2021
INVENTOR(S) : Gendelman et al.

It is certified that error appears in the above-identified patent and that said Letters Patent is hereby corrected as shown below:

In the Specification

Column 1, Line number 21-23, please delete "AG043540, and R56 AI138613 awarded by the National Institutes of Health. The government has certain rights in the invention." and replace with --AG043540, R56 AI138613 and R01 AI158160 awarded by the National Institutes of Health. The government has certain rights in the invention.--

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*